United States Patent
Narimatsu et al.

(10) Patent No.: US 10,352,927 B2
(45) Date of Patent: Jul. 16, 2019

(54) GLYCOFORM DETECTION METHOD AND GLYCOFORM DETECTION DEVICE

(71) Applicant: NATIONAL INSTITUTE OF ADVANCED INDUSTRIAL SCIENCE AND TECHNOLOGY, Tokyo (JP)

(72) Inventors: Hisashi Narimatsu, Tsukuba (JP); Atsushi Kuno, Tsukuba (JP); Yuzuru Ikehara, Tsukuba (JP); Yasuhiro Hashimoto, Fukushima (JP); Keiro Shirotani, Fukushima (JP); Kiyomitsu Nara, Fukushima (JP); Yoshinobu Kariya, Fukushima (JP); Hiromi Ito, Fukushima (JP); Kyoka Hoshi, Fukushima (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 748 days.

(21) Appl. No.: 14/419,804

(22) PCT Filed: Aug. 9, 2013

(86) PCT No.: PCT/JP2013/071653
§ 371 (c)(1),
(2) Date: Jun. 12, 2015

(87) PCT Pub. No.: WO2014/025013
PCT Pub. Date: Feb. 13, 2014

(65) Prior Publication Data
US 2015/0338396 A1 Nov. 26, 2015

(30) Foreign Application Priority Data
Aug. 10, 2012 (JP) ................ 2012-178722

(51) Int. Cl.
*G01N 33/543* (2006.01)
*G01N 33/536* (2006.01)
*G01N 33/53* (2006.01)
*G01N 33/68* (2006.01)

(52) U.S. Cl.
CPC ........ *G01N 33/5308* (2013.01); *G01N 33/536* (2013.01); *G01N 33/6854* (2013.01); *G01N 2333/42* (2013.01); *G01N 2333/4724* (2013.01); *G01N 2400/00* (2013.01); *G01N 2440/38* (2013.01); *G01N 2496/00* (2013.01)

(58) Field of Classification Search
CPC .......................... G01N 33/543; G01N 33/536
See application file for complete search history.

(56) References Cited

U.S. PATENT DOCUMENTS 5,591,589 A 1/1997 Katoh et al.
2011/0294141 A1 12/2011 Yamashita et al.

FOREIGN PATENT DOCUMENTS

| CN | 102317785 A | 1/2012 | |
|---|---|---|---|
| JP | H07191027 A | 7/1995 | |
| JP | 2010-121980 A | 6/2010 | |
| WO | 03102581 A2 | 12/2003 | |
| WO | WO-03102581 A2 * | 12/2003 | ............. G01N 33/53 |
| WO | WO-2012065182 A2 * | 5/2012 | |

OTHER PUBLICATIONS

Ishikawa, et al., "Guidelines for Management of Idiopathic Normal Pressure Hydrocephalus: Guidelines From the Guidelines Committee of Idiopathic Normal Pressure Hydrocephalus, the Japanese Society of Normal Pressure Hydrocephalus", Neurol Med Chir Suppl (Tokyo) 48, 2008, pp. S1-S23.

Futakawa, et al., "A unique N-glycan on human transferrin in CSF: a possible biomarker for iNPH", Neurobiology of Aging, 33, 2012, 1807-1815.

Shimizu et al., Discrimination of Thyroglobulin from Thyroid Carcinoma Tissue and that from Benign Thyroid Tissues with Use of Competitive Assay between Lectin and Anti-Thyroglobulin Antibody, Rinsho Byori, 2007, vol. 55, No. 5, pp. 428-433.

Matsumoto et al., "Antibody-lectin sandwich enzyme immunoassay for determination of altered asparagine-linked sugar chains in serum transferrin of patients with hepatoma", Chemical Abstracts, 1995, vol. 122, No. 15, Abstract.

Shirotani et al., "High Throughput ELISAs to Measure a Unique Glycan on Transferrin in Cerebrospinal Fluid: A Possible Extension toward Alzheimer's Disease Biomarker Development", International Journal of Alzheimer's Disease, 2011, vol. 8, No. 6, pp. 1-5.

Supplementary European Search Report for European Application No. EP13827110.1 (dated Mar. 21, 2016) (2 pages).

(Continued)

*Primary Examiner* — Tracy Vivlemore
*Assistant Examiner* — Nam P Nguyen
(74) *Attorney, Agent, or Firm* — Lucas & Mercanti, LLP

(57) ABSTRACT

It is intended to develop and provide a method for detecting a particular glycan-isoform rapidly and specifically by a small number of steps. The present invention provides a glycan-isoform detection method comprising quantifying an immune complex formed by the mixing of a test sample with a sugar chain non-reducing terminal residue-binding lectin and an antibody specifically binding to the protein moiety of the glycan-isoform, etc., comparing the obtained amount of the immune complex with the amount of a control immune complex obtained when a control sample is not mixed with the sugar chain non-reducing terminal residue-binding lectin or is mixed with a control protein, and determining the presence or absence of the glycan-isoform of interest in the test sample on the basis of the difference between these amounts.

13 Claims, 18 Drawing Sheets

(56) References Cited

OTHER PUBLICATIONS

Japanese Office Action for Japanese Application No. 2014-529573 dated Feb. 16, 2016.
Chinese Office Action for Chinese Application No. 201380052689.6 dated Feb. 3, 2016.

* cited by examiner

A

B (a)    (b)

(c)    (d)

(e)    (f)

(g)    (h)

(i)

□ : GalNAc
■ : GlcNAc
○ : Gal
● : Man
◆ : Sia

Anti-Muc1 antibody + BSA       Anti-Muc1 antibody + WFA

GLYCOFORM DETECTION METHOD AND GLYCOFORM DETECTION DEVICE

CROSS-REFERENCE TO RELATED APPLICATIONS

This application is a 371 of PCT/JP2013/071653, filed Aug. 9, 2013, which claims the benefit of Japanese Patent Application No. 2012-178722, filed Aug. 10, 2012.

TECHNICAL FIELD

The present invention relates to a glycan-isoform detection method that can detect a glycoprotein isoform (glycan-isoform) having a particular sugar chain, and a glycan-isoform detection apparatus that employs the method.

BACKGROUND ART

In developed countries including Japan in which the society is aging, age-related diseases show an increasing tendency. Among them, the number of patients with dementia typified by Alzheimer's disease is significantly increasing and has become a major social problem because of involving disturbance in daily life, increased care burden on families or the like, etc.

Incidentally, idiopathic normal pressure hydrocephalus (iNPH; hereinafter, referred to as "iNPH") is known as a disease that exhibits symptoms similar to those of Alzheimer's disease. According to epidemiological studies, the number of dementia patients in Japan exceeds 3,000,000 people, among which, by estimate, Alzheimer's disease patients account for more than half and idiopathic normal pressure hydrocephalus (iNPH) patients account for 310,000 people. Both the diseases have common symptoms of dementia and ventricular dilatation, but largely differ in that the curative therapy of Alzheimers disease has not yet been established, whereas iNPH is "treatable dementia" that can be cured by operations such as shunting (Non Patent Literature 1). Nonetheless, the number of operations of this shunting remains at yearly 1,200 cases in Japan. Among the 310,000 potential patients, patients who have undergone the operation are only 0.4% on a single-year basis. Examples of the reason therefor include the misdiagnosis of many iNPH patients with Alzheimer's disease because a convenient and reliable diagnosis method to distinguish iNPH patients from Alzheimer's disease patients has not been established.

Although the cause of iNPH is unknown, an excess of spinal fluid caused by the abnormal absorption of spinal fluid is suspected. In iNPH, excessive spinal fluid compress the brain. Thus, a method (tap test) which involves removing a large amount of spinal fluid by lumbar puncture and using the presence or absence of the resulting alleviation of the symptoms of the compressed brain as an index is adopted for the definitive diagnosis of iNPH. This method, however, is highly invasive and also has a high false-negative rate. In addition, since most of iNPH patients are elderly persons, only a small amount of spinal fluid is collected due to lumbar deformity, often making the diagnosis itself impossible. Hence, the development of a reliable diagnosis method to distinguish both the diseases is an important medical theme (Non Patent Literature 1).

To solve these problems, a method which involves searching for a glycoprotein that is contained in a body fluid and is highly correlated with a particular disease, and using the glycoprotein as a diagnostic marker for determining the presence of the disease has received attention in recent years. Most of proteins in body fluids are modified with sugar chains, and these sugar chains often have structures specific for organs, tissues, cell species, or disease conditions of their origins. Specifically, it is known that even the same proteins have distinctive sugar chains when derived from different organs or tissues. Hence, abnormality in a particular organ can be detected by use of a glycan-isoform.

For example, Patent Literature 1 discloses spinal fluid-derived glycoprotein transferrin-1 (Tf-1) (glycan-isoform characteristic of spinal fluid) having a sugar chain containing terminal N-acetylglucosamine (GlcNAc) as a diagnostic marker capable of distinguishing iNPH from Alzheimer's disease (Non Patent Literature 2). The method disclosed therein can distinguish iNPH from Alzheimer's disease with high accuracy by detecting Tf-1 having the sugar chain from spinal fluid. Also, the method can distinguish iNPH from other dementia types such as frontotemporal dementia and dementia with Lewy bodies. Meanwhile, Tf-1 as well as a transferrin isoform having a different sugar chain structure (transferrin-2: Tf-2) is present in spinal fluid. Heretofore, the identification of a protein moiety using an antibody and the identification of a sugar chain moiety using a lectin have had to be carried out in separate steps in order to detect a particular glycan-isoform in the spinal fluid in which these glycan-isoforms coexist with each other. Such a detection method is poorly efficient and is also inferior in rapidness. Further problems thereof are that full automation is difficult due to complicated procedures with many steps and a high-throughput process cannot be achieved.

CITATION LIST

Patent Literature

Patent Literature 1: JP Patent Publication (Kokai) No. 2010-121980 A (2010)

Non Patent Literature

Non Patent Literature 1: Ishikawa et al., 2008, Neurologia medico-chirurgica, 48, Supplement (Guidelines for iNPH)

Non Patent Literature 2: Futakawa et al., 2012, Neurobiol Aging, 33: 1807-15

SUMMARY OF INVENTION

Technical Problem

An object of the present invention is to develop and provide a method for detecting a particular glycan-isoform rapidly and specifically by a small number of steps.

Solution to Problem

The present inventors have conducted diligent studies to attain the object and consequently found a phenomenon in which the binding of a lectin to sugar chain non-reducing terminal residue(s) in a glycoprotein inhibits the antigen-antibody reaction of an antibody specifically recognizing the protein moiety of the glycoprotein. In addition, the present inventors have also revealed that this phenomenon is not a special phenomenon that occurs only when a particular limited type of antibody is used, but is a universal phenomenon that is found in general antibodies recognizing the protein moieties of glycoproteins.

The competition of a lectin with an antibody for a glycoprotein has also been reported previously. For example, Suzuki et al. have quantified fucosylated α-fetoprotein (AFP-L3) by use of monoclonal antibodies and a lectin (Suzuki, Y., et al., Br J Cancer, 1987, 55 (2): 147-52). This quantification method is a method which involves adding LCA lectin (*Lens culinaris* agglutinin) to a sandwich ELISA system using two types of anti-AFP monoclonal antibodies (one for capture and the other for detection), and detecting the inhibition of antibody binding to AFP-L3 by the binding of LCA to AFP-L3 as the amount of reduction in ELISA signal to thereby quantify AFP-L3 in total AFP. This method can quantify a glycan-isoform (AFP-L3) having core fucose without the separation thereof from other glycan-isoforms.

Alternatively, Kato et al have disclosed that in the detection of core fucose-containing glycoprotein thyroglobulin that appears in thyroid cancer, the binding of some anti-thyroglobulin monoclonal antibodies to their antigens is inhibited by the presence of AAL lectin binding to core fucose (Kato, R. et al., Journal of Kagawa Prefectural College of Health Science, 2003. 5: 39-44).

The binding inhibition of antibody by the LCA or AAL lectin reportedly takes place under a mechanism where the lectin binds to fucose branched from a sugar directly attached to an amino acid, i.e., core fucose in a core sugar chain, in a glycan-isoform so that an antigen epitope positioned near the core sugar chain is obscured, resulting in its reduced reactivity with the antibody (Suzuki, Y., et al., Br J Cancer, 1987, 55 (2): 147-52). That is, the close proximity of a lectin-binding site to an antigen epitope in a glycoprotein is considered to be important for the inhibition of immune complex formation. In general, a very limited number of antigen epitopes on proteins are obscured by proximal sugar chain-binding lectins, and the majority of monoclonal antibodies can bind to the glycoproteins without competing with the lectins. In fact, monoclonal antibodies whose binding to glycoproteins were inhibited by core fucose-binding lectins among the proximal sugar chain-binding lectins are only two out of 30 clones examined (Taketa K, et al, Tumour Biol, 1998, 19: 318-28).

Meanwhile, it is generally believed in the art that sugar chain non-reducing terminal residue-binding lectins cannot inhibit antigen-antibody reaction, because sugar chain non-reducing terminal residues are distal to proteins. Hence, the competition of a lectin with an antibody for a glycoprotein has been considered as, not a universal phenomenon, but a very special phenomenon that may occur by the combination of only a few proximal sugar chain-binding monoclonal antibodies and proximal sugar chain-binding lectins.

However, the aforementioned phenomenon found by the present inventors is a consequence that has completely overcome the conventional theory. This suggests that a core sugar chain-binding lectin inhibits the binding between a glycoprotein and antibody under a mechanism totally different from that for the previously reported ability of the lectin to inhibit antigen-antibody reaction. The present invention has been completed on the basis of the aforementioned novel phenomenon and provides the followings:

(1) A method for detecting a glycan-isoform of interest in a test sample, comprising:

a lectin mixing step of mixing the test sample with a sugar chain non-reducing terminal residue-binding lectin which binds to the whole or a portion of sugar chain non-reducing terminal residue(s) in the sugar chain moiety of the glycan-isoform of interest; an antibody mixing step of mixing the test sample with an antibody specifically binding to the protein moiety of the glycan-isoform of interest, or an active fragment thereof; a complex quantification step of quantifying an immune complex of the antibody or the active fragment thereof and the glycan-isoform of interest after the lectin mixing step and the antibody mixing step; and a determination step of determining the presence or absence of the glycan-isoform of interest in the test sample on the basis of the difference between the amount of the immune complex and the amount of a control immune complex obtained when a control sample is not mixed with the sugar chain non-reducing terminal residue-binding lectin or is mixed with a control protein.

(2) The glycan-isoform detection method according to (1), wherein the determination step involves determining that the glycan-isoform of interest is present in the test sample when the amount of the immune complex is statistically significantly lower than the amount of a control immune complex.

(3) The glycan-isoform detection method according to (1) or (2), wherein the antibody mixing step is carried out after the lectin mixing step.

(4) The glycan-isoform detection method according to (1) or (2), wherein the lectin mixing step is carried out after the antibody mixing step.

(5) The glycan-isoform detection method according to (1) or (2), wherein the lectin mixing step and the antibody mixing step are carried out at the same time.

(6) The glycan-isoform detection method according to any of (1) to (5), wherein the test sample is a body fluid or a tissue section.

(7) An apparatus for detecting a glycan-isoform of interest, comprising: a reaction part of mixing a sugar chain non-reducing terminal residue-binding lectin which binds to the whole or a portion of sugar chain non-reducing terminal residue(s) in the sugar chain moiety of the glycan-isoform to be detected, an antibody specifically binding to the protein moiety of the glycan-isoform to be detected, or an active fragment thereof, and a test sample to cause the binding reaction of the glycan-isoform with the sugar chain non-reducing terminal residue-binding lectin or the antibody or the active fragment thereof; a detection part of quantitatively detecting an immune complex of the glycan-isoform and the antibody or the active fragment thereof formed in the reaction part; and a comparative determination part of comparing the amount of the immune complex obtained in the detection part with the amount of a control immune complex obtained when a control sample is not mixed with the sugar chain non-reducing terminal residue-binding lectin or is mixed with a control protein, and determining the presence or absence of the glycan-isoform of interest in the test sample on the basis of the comparison results.

(8) The glycan-isoform detection apparatus according to (7), wherein the reaction part comprises a mixing order control unit which controls the order in which the sugar chain non-reducing terminal residue-binding lectin, the antibody or the active fragment thereof, and the test sample are mixed.

(9) The glycan-isoform detection apparatus according to (7) or (8), wherein the determination part determines that the glycan-isoform is present in the test sample when the amount of the immune complex obtained in the detection part is statistically significantly lower than the amount of a control immune complex.

(10) The glycan-isoform detection apparatus according to any of (7) to (9), wherein the test sample is a body fluid or a tissue section.

(11) A method for identifying a glycan-isoform, comprising identifying the glycan-isoform using a glycan-isoform detection method according to any of (1) to (6).

The contents described in the specification and/or drawings of Japanese Patent Application No. 2012-178722, to which the present application claims priority, is incorporated herein.

Advantageous Effects of Invention

The glycan-isoform detection method of the present invention enables a glycan-isoform to be detected rapidly, conveniently, and at a high throughput rate by a smaller number of steps than that of a conventional method.

The glycan-isoform detection apparatus of the present invention can automatically detect the glycan-isoform to be detected in a test sample.

BRIEF DESCRIPTION OF DRAWINGS

FIG. 2A shows a trimannosyl core sugar chain. FIGS. 2B(a) to 2B(i) each show an O-glycan core sugar chain. These diagrams also show an amino acid residue attached to each core sugar chain, i.e., an asparagine (Asn) residue attached to the trimannosyl core sugar chain and serine (Ser) or threonine (Thr) residues attached to the O-glycan core sugar chain.

FIG. 4-1 is a diagram showing that the inhibition of immune complex formation by the sugar chain non-reducing terminal residue-binding lectin is based on the sugar chain-specific binding of this lectin to the glycan-isoform.

FIG. 4-2 shows results of gel electrophoresis analysis. In the diagram, Ser represents Tf in serum, Tf represents purified Tf, and AsT represents asialo-Tf. Silver represents silver staining, Tf-Ab represents Western blot using an anti-human Tf antibody, and SSA represents lectin blot using SSA lectin.

FIG. 13-1 shows the detection of serum Tf having α2,6-sialic acid in a human liver section.

FIG. 13-2 is a diagram showing that the inhibition of immune complex formation by SSA lectin depends on sialic acid in immunohistochemistry following the sialidase treatment of a human liver section.

FIGS. 14A and 14B show mirror sections, which are therefore supposed to be in a bilaterally symmetric relationship. Here, the image of FIG. 14B is indicated by a mirror-reversed image for easy comparison.

FIG. 15A shows Tf-2, and FIG. 15B shows Tf-1. The lectins (SSA, PVL, UDA, E4-PHA, and AAL) shown in the diagrams each recognize, as a binding site, a region enclosed in a broken line indicated by an arrow on the sugar chain.

FIG. 16A shows a BSA-treated section, and FIG. 16B shows an SSA-treated section. The arrowheads in the diagrams indicate α2,6-sialylated CEA stained with an antibody. Also, the arrows indicate cells whose cell bodies are densely stained with an anti-CFA antibody (oval region stained pale purple with hematoxylin represents the nucleus of the cell).

DESCRIPTION OF EMBODIMENTS

Figure 1:
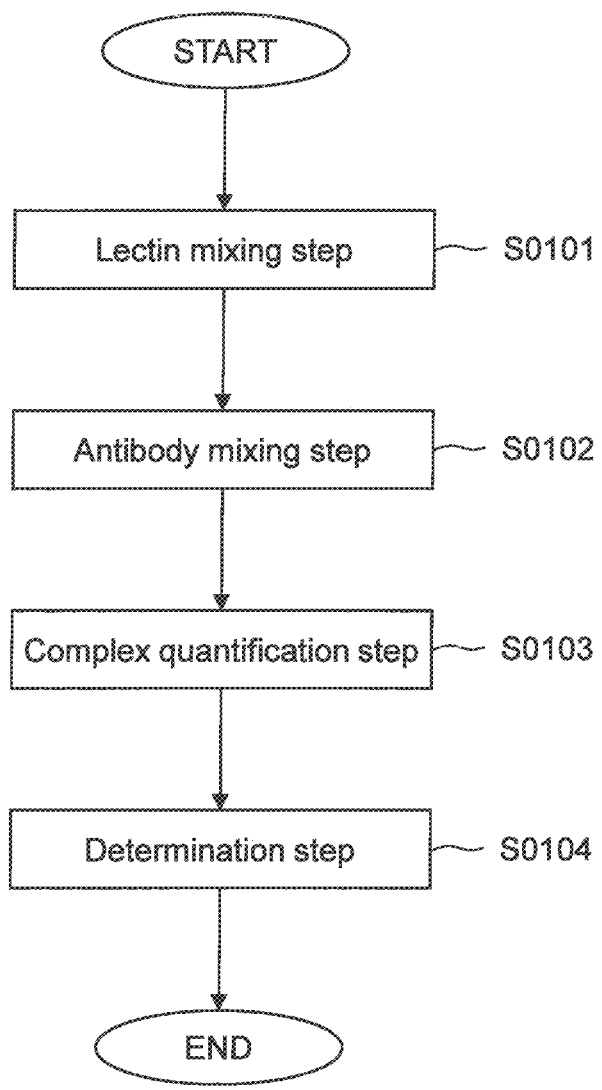
FIG. 1 is a diagram showing the flow of the glycan-isoform detection method of the present invention.

1. Glycan-Isoform Detection Method
1-1. Summary and Definition

The first aspect of the present invention relates to a method for differentially detecting a glycan-isoform of interest in a test sample. The detection method of the present aspect is based on a phenomenon in which a lectin binding to sugar chain non-reducing terminal residue(s) in a glycan-isoform inhibits the antigen-antibody reaction between the glycan-isoform and an antibody specifically recognizing the protein moiety (hereinafter, in the present specification, also referred to as a "core protein") of the glycan-isoform, or an active fragment thereof. The detection method of the present aspect enables the glycan-isoform of interest in a test sample to be detected rapidly, conveniently, and at a high throughput rate by a smaller number of steps than that of a conventional glycan-isoform detection method. The present invention permits, for example, cancer detection based on a cancer-specific glycan-isoform, because 70% of cancer markers are sugar chains. In a conventional method for cancer detection, screening is carried out by detecting only sugar chain moieties. According to the present invention, however, the sugar chain moieties and core proteins can be simultaneously monitored. More rapid and specific cancer detection can therefore be achieved.

In the present specification, the "glycan-isoform" refers to a generic name for individual glycoproteins having various isoforms (isomers) at their sugar chain moieties. Examples thereof include glycoproteins that have identical core proteins and core sugar chains (mentioned later) in their sugar chains and differ in the other sugar chain structures. In the present specification, the "glycan-isoform of interest" refers to a glycan-isoform to be detected from a test sample according to the present aspect. More specific examples thereof include glycan-isoforms that are highly correlated with particular diseases and may serve as markers for disease detection. Since the glycan-isoforms exhibit cell species specificity or tissue specificity, all cell species or tissues can be identified by the identification of the glycan-isoforms.

In the present specification, the "test sample" refers to an object to be tested that is subjected to the detection method of the present aspect and is a substance possibly containing a glycan-isoform. Examples thereof include body fluids, tissues, and cells collected from one or more individuals, and substances therefrom (e.g., tissue suspensions).

In the present specification, the "individual" refers to a vertebrate, preferably a mammal, more preferably a human individual. The individual may be a disease-affected individual having a certain disease, an individual possibly having a disease, or a healthy individual.

In the present specification, the "body fluid" refers to a biological sample in a liquid state possibly containing a glycan-isoform. Examples thereof include blood (including serum, plasma, and interstitial fluid), lymph, spinal fluid, ascitic fluid, pleural effusion, periradicular fluid, lacrimal fluid, nasal discharge, saliva, sputum, urine, vaginal fluid, seminal fluid, and an extract of each tissue or cell. The body fluid is preferably blood, spinal fluid, or lymph. The body fluid described in the present specification encompasses individual-derived solutions possibly containing a glycan-isoform, such as peritoneal lavages obtained using saline or the like. The body fluid used may be directly collected from the individual or may be diluted or concentrated, if necessary, or supplemented with an anticoagulant such as heparin for blood. The body fluid can be collected on the basis of a method known in the art. For example, blood or lymph can be collected according to a blood collection method known in the art. Specifically, peripheral blood, for example, can be collected with a syringe from the vein or the like in a peripheral portion. Alternatively, spinal fluid can be collected by lumbar puncture known in the art. The body fluid may be used immediately after collection or may be used after being cryopreserved or refrigerated for a given time and then treated (e.g., thawed) if necessary.

The "tissue" refers to a tissue constituting the individual. Every tissue corresponds to the test sample described in the present specification without particular limitations.

1-2. Constitution

The flow of the detection method of the present aspect is shown in FIG. 1. As shown in this diagram, the glycan-isoform detection method of the present aspect comprises a lectin mixing step (S0101), an antibody mixing step (S0102), a complex quantification step (S0103), and a determination step (S0104). Although the diagram of FIG. 1 shows the antibody mixing step subsequent to the lectin mixing step for the sake of convenience, these two steps can be carried out in any order. For example, the antibody mixing step may be carried out following the lectin mixing step, or the lectin mixing step may be carried out following the antibody mixing step. Alternatively, the lectin mixing step and the antibody mixing step may be carried out at the same time.

Hereinafter, each step in the glycan-isoform detection method of the present aspect will be described specifically.

(1) Lectin Mixing Step

The "lectin mixing step" (S0101) is the step of mixing the test sample with a sugar chain non-reducing terminal residue-binding lectin which binds to the whole or a portion of sugar chain non-reducing terminal residue(s) in the sugar chain moiety of the glycan-isoform of interest. This step is aimed at allowing the sugar chain non-reducing terminal residue-binding lectin to bind to the whole or a portion of sugar chain non-reducing terminal residue(s) in the sugar chain moiety of the glycan-isoform of interest that may be present in the test sample.

In the present specification, the "sugar chain non-reducing terminal residue(s)" refers to a sugar chain region other than the core sugar chain in the sugar chain moiety of the glycan-isoform. In the present specification, the "core sugar chain" refers to a proximal sugar chain region that contains a sugar directly attached to an amino acid of the protein, in the sugar chain moiety of the glycan-isoform, and is composed of a scaffold sugar chain structure common to various glycan-isoforms. For example, a trimannosyl core sugar chain (Manα1-6(Manα1-3)Manβ1-4GlcNAcβ1-4(+Fucα1-6)GlcNAc) attached to an asparagine residue shown in FIG. 2A corresponds to the core sugar chain of an asparagine (Asn, N)-linked sugar chain (N-glycan). In this trimannosyl core sugar chain, fucose (so-called core fucose) may be attached to GlcNAc directly attached to the amino acid (asparagine residue). Alternatively, examples of the core sugar chain of O-glycan include structures in which one or two sugars are further attached to GalNAc directly attached to serine/threonine residues, i.e., structures (a) to (i) shown in FIG. 2B, specifically, 9 types of core sugar chains: (a) Siaα2-6GalNAc, (b) Galβ1-3GalNAc, (c) GlcNAcβ1-6(Galβ1-3)GalNAc, (d) GlcNAcβ1-3GalNAc, (e) GlcNAcβ1-6(GlcNAcβ1-3)GalNAc, (f) GalNAcα1-3GalNAc, (g) GlcNAcβ1-6GalNAc, (h) GalNAcα1-6GalNAc, and (i) Galα1-3GalNAc.

In the present specification, the "sugar chain non-reducing terminal residue-binding lectin" refers to a lectin that recognizes and binds to the whole or a portion of the sugar chain non-reducing terminal residue(s). The sugar chain non-reducing terminal residue-binding lectin is not limited by its type as long as the lectin binds to the whole or a portion of the sugar chain non-reducing terminal residue(s). When the sugar chain non-reducing terminal residue is, for example, α2,6-sialic acid (sialic acid α2,6-linked galactose/GalNAc structure), examples thereof include α2,6-sialic acid-binding lectin. Specifically, for example, *Sambucus sieboldiana*-derived agglutinin SSA lectin, *Sambucus nigra*-derived agglutinin SNA lectin, and *Trichosanthes japonica*-derived type I agglutinin TJA-1 lectin correspond thereto. When the sugar chain non-reducing terminal residue is α2,3-sialic acid (sialic acid α2,3-linked galactose structure), examples thereof include α2,3-sialic acid-binding lectin. Specifically, for example, *Maackia amurensis*-derived agglutinin MAL lectin corresponds thereto. In the case of a glycan-isoform having a terminal sugar galactose or GalNAc as a sugar chain non-reducing terminal residue, examples thereof include terminal galactose/GalNAc-binding lectin. Specifically, for example, *Erythrina cristagalli*-derived agglutinin ECA lectin, *Ricinus communis*-derived agglutinin RCA120 lectin, *Bauhinia purpurea*-derived agglutinin BPL lectin, the *Trichosanthes japonica*-derived agglutinin TJA-II lectin, *Wisteria floribunda*-derived agglutinin WFA lectin, and agglutinin ACA lectin correspond thereto. In the case of a glycan-isoform having a terminal sugar GlcNAc as a sugar chain non-reducing terminal residue, examples thereof include terminal GlcNAc-binding lectin. Specifically, for example, *Griffonia simplicifolia* (family Fabaceae)-derived agglutinin GSL-II lectin and *Agaricus bisporus*-derived agglutinin ABA lectin correspond thereto. In the case of a glycan-isoform having a repeat structure of lactosamine (Galβ1,4GlcNAc) as a sugar chain non-reducing terminal residue evolved on a trimannose core structure, examples thereof include polylactosamine-binding lectin. Specifically, for example, *Lyciper-* sicon esculentum-derived agglutinin LEL lectin and Solanum tuberosum-derived agglutinin STL lectin correspond thereto. In the case of a glycan-isoform having fucose contained in ABO and Lewis blood group antigens as a sugar chain non-reducing terminal residue, examples thereof include blood group antigen fucose-binding lectin. Specifically, for example, *Lotus tetragonolobus*-derived agglutinin LTL lectin and *Ulex europaeus*-derived agglutinin UEA-I lectin correspond thereto. Commercially available lectins may be used as these lectins. For example, 300177 from Seikagaku Biobusiness Corp. or J1001014 from Medical & Biological Laboratories Co., Ltd. (MBL) can be used as SSA lectin. L6890 Lectin from *Sambucus nigra* (elder) from Sigma-Aldrich Corp. can be used as SNA lectin. 300186 from Seikagaku Biobusiness Corp. can be used as TJA-1 lectin.

The mixing conditions are not particularly limited as long as the sugar chain non-reducing terminal residue-binding lectin can bind to the glycan-isoform of interest under the conditions. They can be mixed in a buffer having an appropriate salt concentration and pH. When the test sample is a liquid sample such as a body fluid, the sugar chain non-reducing terminal residue-binding lectin may be directly mixed into the body fluid. The amount of the sugar chain non-reducing terminal residue-binding lectin to be mixed with the test sample can be appropriately determined according to the quantity of the test sample. Usually, a large excess of the sugar chain non-reducing terminal residue-binding lectin as a molar ratio to the total amount of lectin-binding site-containing glycoproteins that may be present in the test sample is added. In the case of detecting, for example, a serum glycan-isoform Tf-2 from the test sample, the sugar chain non-reducing terminal residue-binding lectin can be added such that not only α2,6-sialic acid epitopes carried by Tf2 but all of epitopes in α2,6-sialic acid-containing glycoproteins are saturated with α2,6-sialic acid-binding lectin such as SSA. Specifically, for example, for the assay of Tf-2 in spinal fluid, 10 µg of SSA lectin can be mixed with 0.5 µL of spinal fluid. The total concentration of α2,6-sialic acid-containing glycoproteins in the spinal fluid is 0.2 to 0.3 µg/0.5 µL. Also, the concentration of Tf-2 in the spinal fluid is approximately 0.01 µg/0.5 µL.

(2) Antibody Mixing Step

The "antibody mixing step" (S0102) is the step of mixing the test sample with an antibody specifically binding to the core protein of the glycan-isoform of interest, or an active fragment thereof. This step is aimed at mixing the antibody or the active fragment thereof (hereinafter, also collectively referred to as an "antibody, etc.") with the test sample to thereby allow the antibody, etc. to bind to the core protein of the glycan-isoform of interest that may be present in the test sample.

The antibody, etc. used in this step is an anti-core protein antibody, etc. that recognizes any antigen epitope present on the core protein of the glycan-isoform of interest and specifically binds to the epitope. When the glycan-isoform of interest is, for example, spinal fluid-derived transferrin (Tf-2), examples thereof include anti-transferrin antibodies that specifically recognize and bind to the core protein transferrin, and active fragments thereof.

In the present specification, the "antibody" refers to an immunoglobulin, a chimeric antibody, a humanized antibody, or a synthetic antibody.

When the antibody is an immunoglobulin, this antibody may be a polyclonal antibody which is a cluster of many types of antibodies binding to the core protein of the glycan-isoform of interest or may be a monoclonal antibody which is a group of clone antibodies that recognize a particular epitope. The immunoglobulin can be of any class, for example, IgG, IgE, IgM, IgA, IgD, and IgY, or of any subclass, for example, IgG1, IgG2, IgG3, IgG4, IgA1, and IgA2.

The "chimeric antibody" refers to an antibody obtained from an antibody derived from a certain organism species by the replacement of its constant regions with the constant regions of an antibody derived from another organism species. In the present invention, the chimeric antibody means an antibody obtained from an antibody derived from a non-human animal by the replacement of its constant regions with the constant regions of an appropriate antibody derived from a human. For example, an antibody obtained from a mouse anti-human transferrin monoclonal antibody by the replacement of its constant regions with the constant regions of a human antibody corresponds thereto.

The "humanized antibody" refers to a mosaic antibody in which CDRs (i.e., CDR1, CDR2, and CDR3) derived from an antibody derived from a certain organism species (usually, a non-human antibody, for example, a mouse antibody) are artificially combined with FRs (i.e., FR1, FR2, FR3, and FR4) and constant regions of a human antibody. Such a humanized antibody is also called CDR-grated antibody (Nature (1986) Vol. 321, 522).

The "synthetic antibody" refers to an antibody or an antibody fragment newly synthesized using, for example, a recombinant DNA method. Specifically, a monomeric polypeptide molecule comprising one or more $V_L$ regions and one or more $V_H$ regions of the antibody of the present invention artificially linked via a linker peptide or the like having an appropriate length and sequence, or a multimeric polypeptide thereof corresponds thereto, though the synthetic antibody is not limited thereto. For example, a single chain fragment of variable region (scFv) (see Pierce Catalog and Handbook, 1994-1995, Pierce Chemical Co., Rockford, Ill.) corresponds to the monomeric polypeptide molecule. Also, for example, a diabody, a triabody, or a tetrabody corresponds to the multimeric polypeptide. The diabody refers to a molecule having a structure based on the structure of a scFv dimer (Holliger et al., 1993, Proc. Natl. Acad. Sci. USA 90: 6444-6448). In the diabody, which is a divalent antibody fragment, its two antigen-binding sites do not have to bind to the same epitope and may be bispecific to respectively recognize and specifically bind to different epitopes. The triabody and the tetrabody have trimeric and tetrameric structures, respectively, based on the scFv structure, as with the diabody. The triabody and the tetrabody are trivalent and tetravalent antibody fragments, respectively, and may be multispecific antibodies.

The antibody, etc. used in this step is preferably a monoclonal antibody, or a chimeric antibody, a humanized antibody, or a synthetic antibody equivalent thereto (hereinafter, referred to as a "monoclonal antibody, etc.") in terms of detection sensitivity, detection accuracy, and stably supply. The antibody, etc. used in this step may be the combination of a plurality of monoclonal antibodies, etc. that recognize and bind to different antigen epitopes.

In the present specification, the "active fragment thereof" refers to a partial region of the antibody mentioned above and is a polypeptide chain having activity substantially equivalent to the antigen-specific binding activity of the antibody, or a complex thereof. For example, a polypeptide chain having at least one light chain variable region ($V_L$) and at least one heavy chain variable region ($V_H$), or a complex thereof corresponds thereto. Specific examples thereof include antibody fragments that are formed by the cleavage of immunoglobulins with various peptidases. As a more specific example, Fab, F(ab')$_2$, Fab', or the like corresponds thereto.

The antibody, etc. used in this step may be modified by, for example, glycosylation, acetylation, formylation, amidation, phosphorylation, or PEGylation. The antibody, etc. may be further labeled, as described in the complex quantification step mentioned later.

The antibody, etc. used in this step can be derived from every animal including mammals and bird. Examples thereof include mice, rats, guinea pigs, rabbits, goats, donkeys, sheep, camels, horses, chickens, and humans.

For the conventional glycan-isoform detection method based on the competition of a core sugar chain-binding lectin with an antibody, etc. as mentioned above, it is required that an antigen epitope recognized by the antibody, etc. should be positioned near the core sugar chain due to the obscuring and inhibiting mechanism by lectin binding. By contrast, the antibody, etc. used in this step is free from such positional limitations. Hence, the antibody, etc. may recognize a primary structure (amino acid sequence) present in the core protein or may recognize a higher order structure, such as a secondary structure or a three-dimensional structure, of the core protein.

The antibody, etc. used in this step can be prepared according to a method known in the art. See, for example, Kennet et al., (Ed.) Monoclonal Antibodies, Hybridomas: A New Dimension in Biological Analyses, Plenum Press, New York, 1980. Hereinafter, the method for preparing a polyclonal antibody will be described with reference to a specific example. First, the whole or a portion of the core protein of the glycan-isoform of interest is dissolved as an antigen in a buffer solution to prepare an immunogen solution. If necessary, the antigen may be bound with a carrier protein such as keyhole limpet hemocyanin (KLH), casein, or serum albumin, or an adjuvant may be added thereto for efficient immunization. Examples of the adjuvant include a commercially available Freund's complete adjuvant (FCA) and Freund's incomplete adjuvant (FIA). These adjuvants may be used alone or as a mixture. Next, a mammal, for example, a rat, a mouse, or a rabbit, is immunized with the prepared immunogen solution. The single dose of the immunogen solution is appropriately determined according to the type of the immunized animal, an administration route, etc. Usually, the single dose can contain approximately 50 to 200 µg/animal of the immunogen. Examples of the method for administering the immunogen solution include subcutaneous injection using FIA or FCA, intraperitoneal injection using FIA, and intravenous injection using 0.15 mol/L of sodium chloride. The intervals between immunization shots are not particularly limited, and 2 to 10, preferably 3 or 4 booster shots following initial immunization are performed at intervals of several days to several weeks, preferably 1 to 4 weeks. After the initial immunization, an antibody titer in the serum of the immunized animal is measured by ELISA or the like. After the confirmation that the antibody titer has reached a plateau, the immunogen solution can be intravenously or intraperitoneally injected to the animal for the final immunization. After the immunization, a polyclonal antibody against the protein of interest can be recovered from blood. Alternatively, if a monoclonal antibody is necessary, its preparation can be carried out according to a method known in the art. Hereinafter, preparation examples of the monoclonal antibody and hybridomas producing the monoclonal antibody will be shown.

The hybridomas can be prepared by use of the immunized animal used for preparing the polyclonal antibody. Antibody-producing cells are collected from the immunized animal. Examples of the antibody-producing cells include spleen cells, lymph node cells, and peripheral blood cells. Spleen cells or local lymph node cells are preferred. A generally available established cell line can be used as a myeloma cell line to be fused with the antibody-producing cells. The cell line used preferably has drug selectivity and has the property of being unable to survive in an unfused state in a HAT selective medium (containing hypoxanthine, aminopterin, and thymidine) and being able to grow therein only in a state fused with the antibody-producing cells. Also, the established cell line is preferably derived from an animal of the same species as the immunized animal. Specific examples of the myeloma cell line include P3X63-Ag.8 (ATCC TIB9), P3X63-Ag.8.U1 (JCRB9085), P3/NSI/1-Ag4-1 (JCRB0009), P3x63Ag8.653 (JCRB0028), and Sp2/0-Ag14 (JCRB0029) lines. Next, the prepared antibody-producing cells are fused with the myeloma cell line. The fusion method can be carried out according to a method known in the art (Kohler, G. and Milstein, C., 1981, Methods Enzymol., 73: 3-46). For the cell fusion, the antibody-producing cells and the myeloma cell line can be mixed at a ratio of approximately 1:1 to 20:1 in a serum-free medium for animal cell culture, such as a DMEM or RPMI-1640 medium, and fused with each other through reaction in the presence of a cell fusion promoter. For example, PEG having an average molecular weight of 1500 to 4000 Da can be used as the cell fusion promoter at a concentration of approximately 10 to 80%. If necessary, an aid such as dimethyl sulfoxide may be used in combination therewith in order to enhance fusion efficiency. Alternatively, the antibody-producing cells and the myeloma cell line may be fused with each other using a commercially available cell fusion apparatus that employs electric stimulation (e.g., electroporation) (Nature, 1977, 266: 550-552). Finally, hybridomas producing the anti-tumor cell monoclonal antibody of interest are selected from the cells after the cell fusion treatment. First, the cell suspension is appropriately diluted with, for example, an RPMI1640 medium containing fetal bovine serum and then seeded over a microtiter plate. A selective medium is added to each well where the cells can subsequently be cultured at approximately 37° C. with the selective medium appropriately replaced with a fresh one. In this operation, only hybridomas of the cells able to produce the antibody and the myeloma cell line can be selectively cultured and proliferated by use of the HAT medium. As a result, cells grown from approximately 14 days after the start of culture in the selective medium can be obtained as hybridomas. The presence or absence of the antibody of interest in the culture supernatants of the proliferated hybridomas can be confirmed by screening using enzyme immunoassay (EIA including ELISA), radioimmunoassay (RIA), or the like to finally establish hybridomas as cells producing the monoclonal antibody of interest.

The monoclonal antibody can be recovered by a routine technique. Specifically, for example, a usual cell culture method or an ascites formation method can be adopted for the established hybridomas. The cell culture method involves: culturing the hybridoma in an animal cell culture medium such as an RPMI1640 medium containing 10% fetal bovine serum, a MEM medium, or a serum-free medium, under usual culture conditions (e.g., 37° C. and 5% $CO_2$ concentration) for 2 to 10 days; and obtaining the antibody from the culture supernatant thereof. In the ascites formation method, the hybridoma is intraperitoneally administered at a dose of approximately 10,000,000 cells to an animal of the same species as the mammal from which the myeloma cells are derived, to proliferate the hybridoma in large amounts. One to two weeks later, ascitic fluid or serum is collected. When the purification of the antibody is necessary for these antibody collection methods, the purified monoclonal antibody can be obtained by an appropriately selected method known in the art, such as ammonium sulfate precipitation, ion-exchange chromatography, affinity chromatography, or gel chromatography, or by the combined use of these methods.

Alternatively, a commercially available antibody against the core protein of the glycan-isoform of interest may be used. In the case of preparing the active fragment thereof, the obtained antibody can be cleaved with any of various peptidases such as papain and pepsin.

The mixing conditions are not particularly limited as long as the antibody, etc. can bind to the glycan-isoform of interest under the conditions. Usually, they can be mixed in a buffer having an appropriate salt concentration and pH at which an immune complex can be formed. When the test sample is a liquid sample such as a body fluid, the antibody, etc. may be directly mixed into the body fluid. The amount of the antibody to be mixed with the test sample can be appropriately determined according to the quantity of the test sample.

As mentioned above, this step and the lectin mixing step may be carried out in any order. This is because the competition of the sugar chain non-reducing terminal residue-binding lectin with the antibody, etc. for the glycan-isoform occurs regardless of process sequences; thus the object of the present invention can be attained even if the steps are carried out in any order. For example, when the lectin mixing step is carried out prior to the antibody mixing step, the sugar chain non-reducing terminal residue-binding lectin binds to the whole or a portion of sugar chain non-reducing terminal residue(s) in the glycan-isoform of interest in the test sample to initially form a lectin/glycan-isoform complex. Then, in the antibody mixing step, the antibody, etc. is added so that the competition for the glycan-isoform of interest occurs between the lectin in the lectin/glycan-isoform complex and the antibody, etc. In this case, the binding of the antibody, etc. to the glycan-isoform of interest is inhibited or suppressed, because the majority of the glycan-isoforms of interest are already bound with the sugar chain non-reducing terminal residue-binding lectins. On the other hand, when the antibody mixing step is carried out prior to the lectin mixing step, the antibody, etc. bind to an antigen epitope in the glycan-isoform of interest in the test sample to initially form an immune complex. Then, in the lectin mixing step, the sugar chain non-reducing terminal residue-binding lectin is added so that the competition for the glycan-isoform of interest occurs between the antibody, etc. in the immune complex and the sugar chain non-reducing terminal residue-binding lectin. In this case, the antibody, etc. is competitively eliminated from some of the already formed immune complexes by the added sugar chain non-reducing terminal residue-binding lectin. Alternatively, when the lectin mixing step and the antibody mixing step are carried out at the same time, the competition for the glycan-isoform of interest in the test sample occurs between the sugar chain non-reducing terminal residue-binding lectin and the antibody, etc.

When the antibody mixing step is carried out prior to the lectin mixing step, the partial purification of antigens from the test sample using the antibody, etc. can also be achieved. This is convenient for a test sample, such as serum, containing many contaminant proteins, because the contaminant proteins can be removed before mixing of the sugar chain non-reducing terminal residue-binding lectin. This is also convenient for a test sample containing the glycan-isoform of interest only in a very small amount, because the glycan-isoform can be enriched into an amount necessary for detection. Hence, this process sequence is more preferred than the other orders.

Since the antibody may also have a sugar chain, the sugar chain non-reducing terminal residue-binding lectin and the antibody, which are used as competitors, might bind to each other, thereby increasing background levels. Accordingly, it is desired that the antibody used should be treated in advance with an enzyme such as sialidase, galactosidase, or hexosaminidase to remove the sugar chain epitope of the antibody, or the sugar chain epitope of the antibody should be destroyed in advance through oxidation reaction by periodate oxidation.

(3) Complex Quantification Step

The "complex quantification step" (S0103) is the step of quantifying an immune complex comprising the antibody, etc. and the glycan-isoform of interest after the lectin mixing step and the antibody mixing step. This step is aimed at determining the amount of the immune complex after the competition of the sugar chain non-reducing terminal residue-binding lectin with the antibody, etc.

In the present specification, the "amount of the complex" refers to the amount of a complex (the immune complex or a control immune complex mentioned later) in a sample (the test sample or a control sample mentioned later). This amount may be a relative amount indicated by fluorescence intensity, luminescence intensity, turbidity, absorbance, radiation dose, or concentration or may be an absolute amount such as the weight or volume of the complex contained in the sample.

The quantification of the immune complex is not particularly limited as long as the method can measure the amount of the immune complex. Since the immune complex is a product of antigen-antibody reaction, an immunological detection method is generally preferably applied thereto. Examples of the immunological detection method include enzyme immunoassay (including ELISA and EIA), fluorescent immunoassay, radioimmunoassay (RIA), luminescent immunoassay, a surface plasmon resonance (SPR) method, a quartz crystal microbalance (QCM) method, immunoturbidimetry, latex agglutination immunoassay, latex turbidimetry, immune adherence hemagglutination (IAHA), a particle agglutination method, a gold colloid method, capillary electrophoresis, Western blotting, and an immunohistochemical method (immunostaining method). All of these methods are known in the art and can be performed according to usual methods in the art as a rule. See methods described in, for example, Current protocols in Protein Sciences, 1995, John Wiley & Sons Inc.; Current protocols in Immunology, 2001, John Wiley & Sons Inc.; Sambrook, J. et. al., (2001) Molecular Cloning: A Laboratory Manual Third Ed., Cold Spring Harbor Laboratory Press, Cold Spring Harbor, N.Y.; "Rinsho Byori (clinical pathology in English), extra edition, No. 53, Immunoassay for Clinical Testing—Technology and Application—" edited by the Japanese Society of Laboratory Medicine, The Clinical Pathology Press, 1983; "Enzyme immunoassay" edited by Eiji Ishikawa et al., 3rd edition, Igaku Shoin Ltd., 1987; "Protein, Nucleic Acid and Enzyme, supple. No. 31, Enzyme Immunoassay" edited by Tsunehiro Kitagawa et al., Kyoritsu Shuppan Co., Ltd., 1987; "Radioimmunoassay" edited by Minoru Irie, Kodansha Scientific Ltd., 1974; "Radioimmunoassay 2" edited by Minoru Irie, Kodansha Scientific Ltd., 1979; Real-Time Analysis and Experiment Methods for Biological Substance Interactions edited by Kazuhiro Nagata and Hiroshi Handa, Springer-Verlag Tokyo, Inc., 1988; and Toyosaka Moriizumi and Takamichi Nakamoto, Sensor Engineering, SHOKODO Co., Ltd, 1997.

One example of a preferred quantification method intended for a tissue section includes a method for digitizing the fluorescence intensity of image data obtained by fluorescent immunostaining or the like. On the basis of the results of this quantification, differential analysis can be numerically conducted between the image of a lectin-supplemented sample and the image of a non-supplemented sample in the determination step mentioned later to reveal a site having the inhibition of immune complex formation and the degree of the inhibitory effect.

In the case of quantifying the immune complex by the aforementioned immunological assay method such as enzyme immunoassay, fluorescent immunoassay, radioimmunoassay, luminescent immunoassay, a surface plasmon resonance method, a quartz crystal microbalance method, latex agglutination immunoassay, latex turbidimetry, a particle agglutination method, or a gold colloid method, it is preferred that the antibody, etc. should be immobilized on a solid-phase carrier, or the glycan-isoform in the test sample should be immobilized thereon. A material such as polyethylene, polypropylene, polystyrene, polycarbonate, polyvinyl chloride, polyvinyltoluene, nylon, polymethacrylate, latex, agarose, cellulose, Sepharose, gelatin, glass, a metal (including a magnetic material), or a ceramic can be used for the solid-phase carrier. The solid-phase carrier is not limited by its form. An insoluble carrier in a form such as beads, a microplate, a test tube, a stick, or a test piece can be used. The immobilization of the antibody, etc. or the glycan-isoform onto the solid-phase carrier can be carried out by the binding of the antibody, etc. or the glycan-isoform to the solid-phase carrier according to a method known in the art such as a physical adsorption method, a chemical binding method, or combined use thereof.

As mentioned above, the antibody, etc. can be labeled with any of various labels. Examples of the label used for labeling the antibody, etc. in enzyme immunoassay include labeling enzymes such as alkaline phosphatase, peroxidase (POD), β-galactosidase, urease, catalase, glucose oxidase, lactate dehydrogenase, and amylase, and biotin or (strept) avidin. Examples of the label in fluorescent immunoassay include Alexa®, Alexa Fluoro®, fluorescein isothiocyanate, tetramethylrhodamine isothiocyanate, substituted rhodamine isothiocyanate, dichlorotriazine and isothiocyanate. Examples of the label in radioimmunoassay include $^3$H, $^{125}$I, and $^{131}$I. Examples of the label in luminescent immunoassay include NADH, FMNH2, a luciferase system, a luminol-hydrogen peroxide-POD system, an acridinium ester system, and a dioxetane compound system.

The detection of the immune complex is carried out according to the aforementioned assay method. For example, in enzyme immunoassay, the labeling enzyme is reacted under its optimum conditions with a substrate, and the amount of the reaction product can be measured by an optical method or a colorimetric method, or the like. In fluorescent immunoassay, the fluorescence intensity of the fluorescent material label can be measured. In radioimmunoassay, the radiation dose of the radioactive substance label can be measured. In luminescent immunoassay, the luminescence intensity of the luminescent reaction system can be measured.

The detection of the immune complex may be direct detection or indirect detection. In the case of the direct detection, the antibody, etc. can be labeled. In the case of the indirect detection, a labeled secondary antibody, etc. can be used.

In the case of the direct detection method, for example, the glycan-isoform in the test sample is immobilized on a solid-phase carrier and subjected to the lectin mixing step and the antibody mixing step. In the antibody mixing step, the glycan-isoform is contacted with the labeled antibody, etc. to form an immune complex. Then, unbound labeled antibodies, etc. are washed off. From the amount of the bound labeled antibody or the amount of the unbound labeled antibody, the immune complex can be detected, and the amount thereof can be measured.

In the case of the indirect detection method, the glycan-isoform of interest in the test sample or the lectin/glycan-isoform complex is reacted with the antibody, etc. as a primary antibody (primary reaction) and further reacted with a labeled secondary antibody (secondary reaction). The primary reaction and the secondary reaction may be performed in reverse order or may be performed at the same time. The labeled secondary antibody may specifically recognize and bind to the primary antibody or may recognize and bind to an antigen epitope in the glycan-isoform of interest. A sandwich method (e.g., sandwich ELISA) which involves immobilizing one of two different antibodies, etc. that recognize and bind to different antigen epitopes on the glycan-isoform of interest, labeling the other antibody, etc., and detecting the antigenic protein of interest is preferred as the indirect detection method, because this method is applicable to automation using an existing automatic immunological detection apparatus. After the immune complex formation, proteins other than the immune complex in the test sample and unbound labeled secondary antibodies are washed off. From the amount of the bound labeled secondary antibody or the amount of the unbound labeled secondary antibody, the glycan-isoform of interest in the test sample can be detected, and the amount thereof can be measured.

In the case of using immunoturbidimetry, latex agglutination, latex turbidimetry, immune adherence hemagglutination, or particle agglutination in the detection of the immune complex, the amount of the immune complex can be measured by measuring, as absorbance or turbidity, change in transmitted light or scattering light in a solution based on the amount of formed agglutinates containing the immune complex.

(4) Determination Step

The "determination step" (S0104) is the step of determining the presence or absence of the glycan-isoform of interest in the test sample on the basis of the difference between the amount of the immune complex and the amount of a control immune complex. This step is aimed at determining whether or not the glycan-isoform of interest is present in the test sample on the basis of the results of the complex quantification step.

In the present specification, the "control immune complex" refers to an immune complex that serves as a negative control for the immune complex to be detected and assayed according to the present invention. The control immune complex is obtained when a control sample is subjected to the same steps as those of the detection method of the present invention or when a control sample is not mixed with the sugar chain non-reducing terminal residue-binding lectin or is mixed with a control protein in the lectin mixing step (S0101). For detecting the glycan-isoform of interest with higher accuracy, it is more preferred that the control immune complex obtained when a control sample is mixed with a control protein should be used as a negative control.

In the present specification, the "control sample" refers to a sample for negative control that is used for measuring the amount of a control immune complex and has substantially the same quality and amount as those of the test sample subjected to the detection method of the present invention. When the test sample subjected to the detection of the glycan-isoform is, for example, a liquid sample such as serum, one of two divided portions of the liquid sample is used as the test sample of the present invention and the other portion is used as the control sample. When the test sample subjected to the detection of the glycan-isoform is a solid sample such as a tissue, one of two continuous sections or one of the right and left areas on cut surface is used as the test sample of the present invention and the other portion is used as the control sample.

In the present specification, the "control protein" refers to a protein shown to be unable to bind to the sugar chain moiety of the glycan-isoform of interest and the antibody, etc. used. Examples thereof include proteins having no sugar chain, such as bovine serum albumin (BSA) and human serum albumin (HSA). Alternatively, when the glycan-isoform of interest is a glycan-isoform having an $\alpha$2,6-sialic acid sugar chain, for example, SSA, SNA, or TJA-I lectin, which does not bind to the $\alpha$2,6-sialic acid sugar chain, may be used as the control. The control protein is mixed with the control sample in the same amount as that of the sugar chain non-reducing terminal residue-binding lectin to be mixed with the test sample, as a rule.

In this step, the results of quantifying the immune complex obtained in the preceding complex quantification step is compared with the results of quantifying the control immune complex. On the basis of the difference between these results, the presence or absence of the glycan-isoform of interest in the test sample is determined.

As mentioned above, the sugar chain non-reducing terminal residue-binding lectin is added to the test sample in the lectin mixing step. When the glycan-isoform of interest, i.e., the protein having the particular sugar chain, is present in the test sample, the competition for the binding to the glycan-isoform occurs between the antibody, etc. having an antigen epitope in the protein moiety and the sugar chain non-reducing terminal residue-binding lectin. As a result, the binding of the antibody, etc. is inhibited or suppressed by the sugar chain non-reducing terminal residue-binding lectin bound with the particular sugar chain in the glycan-isoform, i.e., the lectin/glycan-isoform complex. By contrast, the sugar chain non-reducing terminal residue-binding lectin is not added to the control sample, or the control protein is added thereto instead in the lectin mixing step. In this case, a competitor of the antibody, etc. for the binding to the glycan-isoform of interest in the sample is absent. Hence, when the transferrin glycan-isoform of interest is present in the test sample, the amount of the immune complex is relatively lower than the amount of a control immune complex. In this step, the presence or absence of the transferrin glycan-isoform of interest in the test sample is determined on the basis of this difference between the amount of the immune complex and the amount of a control immune complex. For the determination, as mentioned above, the transferrin glycan-isoform of interest is confirmed to be present in the test sample when the amount of the immune complex is relatively lower than the amount of a control immune complex. Whether or not the amount is relatively lower is determined on the basis of whether or not the amount of the immune complex is quantitatively lower than the amount of a control immune complex, more preferably, is statistically significantly lower than the amount of a control immune complex. In the present specification, the term "statistically significantly" means that there is a significant difference when the difference between the amount of the immune complex and the amount of a control immune complex is statistically processed. A testing method known in the art capable of determining the presence or absence of significance can be appropriately used as a testing method for the statistical processing. For example, the student's t test or multiple comparison test method can be used. Specifically, examples of the significant difference include difference with a significance level smaller than 5%, 1%, or 0.1%. Thus, it can be determined that: the transferrin glycan-isoform of interest is present in the test sample when the amount of the immune complex is statistically significantly lower than the amount of a control immune complex; and the transferrin glycan-isoform of interest is absent in the test sample when both the amounts have no statistically significant difference.

Incidentally, other glycan-isoforms having merely the same core protein as that of the transferrin glycan-isoform of interest may also be present in the sample. The antibody, etc. may bind to such a glycan-isoform to form an immune complex. This immune complex is formed in the same amounts between the test sample and the control test sample as a rule and thereby canceled, having no influence on the determination in this step.

1-3. Method for Identifying Glycan-Isoform

The glycan-isoform detection method of the present invention can also be used as a method for identifying a glycan-isoform. For example, as to various glycan-isoforms known in the art, information on combinations of sugar chain non-reducing terminal residue-binding lectins and antibodies, etc. capable of detecting the glycan-isoforms is collected. Next, a sample containing a glycan-isoform of unknown type is divided into two portions. The lectins and the antibodies are added to one of the portions (for analyte), and only the antibodies are added to the other portion (for control). The amounts of immune complexes formed for analyte and for control are compared. A combination of a sugar chain non-reducing terminal residue-binding lectin and an antibody, etc. by which the amount of the immune complex for analyte is relatively lower than the amount of the immune complex for control is detected. A glycan-isoform corresponding to this combination can be determined as the glycan-isoform of unknown type contained in the sample.

In the case of applying the present invention to the large-scale screening of various glycan-isoforms known in the art, antibody arrays can be used. A glycan-isoform sample associated with a particular disease is divided into two portions. Sample sets for comparison are prepared with and without the addition of a lectin to be examined. These samples are overlaid to antibody arrays of the same lots, and a glycan-isoform that exhibits reduction in signal by the addition of the lectin is identified. When this reduction in signal varies depending on the particular disease, this glycan-isoform is identified as a disease marker. Also, a lectin for future screening is revealed.

1-4. Effect

The glycan-isoform detection method of the present invention can detect a glycan-isoform rapidly and highly accurately by a smaller number of steps than that of a conventional method. Moreover, the glycan-isoform detection method of the present invention permits automated detection of the glycan-isoform of interest in a test sample.

Glycoproteins having tumor-associated carbohydrate antigens are target molecules important for cancer detection. Most of anti-tumor-associated carbohydrate antibodies for use in the pathological diagnosis recognize only sugar chain moieties and do not recognize core proteins. In this case, false positivity is a problem such that other proteins having the sugar chains are also detected. However, the present invention can circumvent the false positivity and enhance the accuracy of cancer diagnosis.

2. Glycan-Isoform Detection Apparatus 2-1. Summary

The second aspect of the present invention relates to a glycan-isoform detection apparatus. The detection apparatus of the present aspect is an apparatus in which the glycan-isoform detection method described in the first aspect is systematized. This apparatus is aimed at rapidly detecting a glycan-isoform to be detected in a test sample. In addition, the apparatus can be automated and as such, can detect or identify the glycan-isoform of interest at a low cost and a high throughput rate.

2-2. Constitution

The glycan-isoform detection apparatus of the present aspect comprises (1) a reaction part, (2) a detection part, and (3) a comparative determination part. Hereinafter, the constitution of each part will be described specifically.

(1) Reaction Part

The "reaction part" is the part of executing the lectin mixing step and the antibody mixing step in the glycan-isoform detection method of the first aspect and is constituted such that a sugar chain non-reducing terminal residue-binding lectin which binds to the whole or a portion of sugar chain non-reducing terminal residue(s) in the sugar chain moiety of the glycan-isoform to be detected, an antibody, etc. specifically binding to the core protein of the glycan-isoform to be detected, and a test sample are mixed to cause the binding reaction of the glycan-isoform with the sugar chain non-reducing terminal residue-binding lectin or the antibody, etc. Specifically, the reaction part is aimed at forming an immune complex or a lectin/glycan-isoform complex through the competition of the sugar chain non-reducing terminal residue-binding lectin with the antibody, etc. for the glycan-isoform of interest that may be contained in the sample.

The reaction part has a reaction vessel where the mixing of the lectin, the antibody, etc., and the sample and the binding reaction are performed. The reaction vessel is not particularly limited by its shape as long as the binding reaction can be achieved. Examples thereof include hollow containers (including tub-shaped, groove-shaped, hole-shaped, and well-shaped containers), tubular containers (including capillary containers), and planar containers (including plate-like containers, the surface of spherical containers, etc.). The reaction vessel is not particularly limited by its material as long as the material does not inhibit or suppress the binding reaction between the sugar chain non-reducing terminal residue-binding lectin or the antibody, etc. and the test sample and is not altered by the sugar chain non-reducing terminal residue-binding lectin, the antibody, etc., or the test sample. Examples thereof include glass, plastics, synthetic rubbers, ceramics, metals, plant fibers (including paper), and polymer gels (including gelatin, agar, and super absorbent polymers).

The reaction part can comprise a mixing order control unit.

The "mixing order control unit" is constituted so as to control the order in which the sugar chain non-reducing terminal residue-binding lectin, the antibody, etc., and the test sample are mixed in the reaction vessel.

Also, the reaction part may comprise a lectin storage unit, a lectin introduction unit, an antibody storage unit, an antibody introduction unit, a sample storage unit, a sample introduction unit, or a stirring unit.

The "lectin storage unit" is constituted so as to store the lectin for use in the binding reaction.

The "lectin introduction unit" is constituted so as to introduce the lectin from the lectin storage unit into the reaction vessel according to the need.

The "antibody storage unit" is constituted so as to store the antibody, etc. for use in the binding reaction.

The "antibody introduction unit" is constituted so as to introduce the antibody from the antibody storage unit into the reaction vessel according to the need.

Specific examples of the "lectin storage unit" and the "antibody storage unit" include storage tanks. Specific examples of the "lectin introduction unit" and the "antibody introduction unit" include introduction tubes and valves.

The method, for example, for mixing the sugar chain non-reducing terminal residue-binding lectin, the antibody, etc., and the test sample in the reaction part can be carried out according to the steps described in the glycan-isoform detection method of the first aspect as a rule. A solution containing the immune complex formed in the reaction part is sent to the next detection part.

(2) Detection Part

The "detection part" is the part of executing the complex quantification step in the glycan-isoform detection method of the first aspect and is constituted such that the immune complex of the glycan-isoform and the antibody, etc. formed in the reaction part is quantitatively detected.

The detection part has a complex quantification unit which quantifies the amount of the immune complex. The complex quantification unit differs depending on the immune complex quantification method performed in the detection part. The detection part can comprise, for example, a luminometer or the like for quantifying the amount of the complex as fluorescence intensity or luminescence intensity, a spectrophotometer, an absorptiometer, or the like for quantifying the amount of the complex as turbidity or absorbance, a scintillation counter or the like for quantifying radiation, an SPR measuring instrument for quantifying the amount of the complex by the surface plasmon resonance method, or a QCM measuring instrument for quantifying the amount of the complex by the quartz crystal microbalance method. The detection part may comprise two or more immune complex quantification units. In the detection part, the amount of the immune complex is obtained as numerical information (e.g., a measurement value) in the complex quantification unit as a rule.

When the reaction vessel in the reaction part comprises a complex quantification unit, the reaction part and the detection part may be unified.

The immune complex quantification method in the detection part can be carried out according to the method described in the complex quantification step in the glycan-isoform detection method of the first aspect as a rule. The information on the amount of the immune complex obtained in the detection part is output to the next comparative determination part.

(3) Comparative Determination Part

The "comparative determination part" is the part of executing the determination step in the glycan-isoform detection method of the first aspect and is constituted such that the amount of the immune complex obtained in the detection part is compared with the amount of a control immune complex obtained when a control sample is not mixed with the sugar chain non-reducing terminal residue-binding lectin or is mixed with a control protein, and the presence or absence of the glycan-isoform of interest in the test sample is determined on the basis of the comparison results.

In this context, the amount of a control immune complex can be determined in a reaction part for a control sample and a detection part for a control sample that are disposed separately from the reaction part and the detection part and have similar configurations thereto, in the glycan-isoform detection apparatus of the present aspect. Alternatively, the amount of a control immune complex may be determined in the reaction part and the detection part before or after the quantification of the amount of the immune complex derived from the test sample. In the latter constitution, the reaction part and the detection part can be thoroughly washed with water, a buffer, or the like before or after each quantification operation such that the immune complex derived from the test sample is not mixed with the control immune complex derived from the control sample.

The comparative determination part has a comparison unit, a determination unit, and a display unit.

The "comparison unit" compares information on the amount of the immune complex and information on the amount of a control immune complex obtained from the detection part (or the detection part for a control sample), determines whether or not the amount of the immune complex is relatively lower than the amount of a control immune complex, more specifically, for example, is statistically significantly lower than the amount of a control immune complex, in the presence of the difference between these amounts, and outputs the results as information on comparison results to the determination unit. The information on comparison results may be output, if necessary, to the display unit mentioned later.

The "determination unit" determines the presence or absence of the glycan-isoform of interest in the test sample on the basis of the information on comparison results obtained from the comparison unit, and outputs the information on determination results to the display unit. The comparison unit and the determination unit are each composed of, for example, hardware such as a computer and appropriate software such as an application for analysis.

The "display unit" displays the information on determination results obtained from the determination unit and, if necessary, the information on comparison results obtained from the comparison unit. The display unit is composed of, for example, a monitor.

The method for comparing the amount of the immune complex with the amount of a control immune complex in the comparative determination part, and the method for determining the presence or absence of the glycan-isoform of interest in the test sample on the basis of the comparison results can be carried out according to the methods described in the determination step in the glycan-isoform detection method of the first aspect.

2-3. Effect

The glycan-isoform detection apparatus of the present invention can detect a glycan-isoform rapidly and highly accurately. Moreover, when the type of a glycoprotein itself is unknown, the glycan-isoform detection apparatus of the present invention can also be applied as a glycan-isoform identification apparatus for identifying the glycoprotein.

The glycan-isoform detection apparatus of the present invention permits automated detection of the glycan-isoform of interest in a test sample.

EXAMPLES

Example 1: Inhibition of Immune Complex Formation by Sugar Chain Non-Reducing Terminal Residue-Binding Lectin (Purpose)

Each lectin binding to sugar chain non-reducing terminal residue(s) was tested for its inhibitory effect on immune complex formation.

(Method)

Since some capture antibodies for use in ELISA have sialic acid, background levels may be increased due to the binding of SSA lectin thereto. For this reason, a capture antibody was treated in advance with periodate to chemically modify (destroy) the sialic acid. Specifically, a rabbit anti-human Tf antibody (Cappel #55045) was treated with sodium periodate (final concentration: 1 mM) at 4° C. for 18 hours. After the reaction, glycine (final concentration: 1 M) was added thereto. The antibody after desalting was immobilized as a periodate-treated antibody onto a plate. Specifically, the antibody (3.2 mg/mL) was diluted to 1:250 with 0.05 M sodium bicarbonate (pH 9.6) and added at a concentration of 100 μL/well to a plate for ELISA (NUNC, 445101), which was then left standing overnight at 4° C. Each well was washed three times with a buffer of Tris buffered saline (TBS) supplemented with 0.05% Tween 20 (TBST), and blocked at 4° C. for 6 hours or longer with 0.4% Block Ace (Snow Brand Milk Products Co., Ltd., UK-B80)-TBS. Each lectin (final concentration: 186 nM) or bovine serum albumin (85040C, Sigma-Aldrich Corp.) as a negative control (final concentration: 186 nM) was added to 0.5 μL of spinal fluid and reacted at room temperature for 1 hour. Then, the reaction mixture is added to the antibody-coated plate and reacted at room temperature for 1 hour. Each well was washed three times with TBS containing 0.05% Tween 20 (TBST), followed by reaction with a goat anti-human transferrin HRP-conjugated antibody (A80-128P, Bethyl Laboratories, Inc.; hereinafter, abbreviated to a "goat anti-human Tf-HRP antibody") (0.1 μg/mL) for detection. Each well was washed three times with TBST. Then, a coloring reagent TMB Microwell Peroxidase substrate (50-76-00, KPL, Kirkegaard & Perry Laboratories, Inc.) was prepared according to the protocol of the reagent kit and added at a concentration of 100 μL/well to the plate, which was then left standing at room temperature for 10 minutes. The reaction was terminated by the addition of 1 N HCl. Then, the absorbance was measured at 450 nm using a microplate reader (Model 680, Bio-Rad Laboratories, Inc.). The total amount of Tf was determined by the assay of an SSA-non-supplemented or BSA-supplemented sample.

As the lectin to be added, SSA lectin (300177, Seikagaku Corp.) was used for Tf-2 or serum Tf (T4382, SIgma-Aldrich Corp.) mentioned later, and *Psathyrella Velutina* (PVL) lectin (165-17591, Wako Pure Chemical Industries, Ltd.), *Urtica dioica* agglutinin (UDA), lectin (BA80051, COSMO BIO Co., Ltd.). AAL lectin (J101, J-Oil Mills, Inc.), or E4-PHA lectin (J111, J-Oil Mills, Inc.) was used for Tf-1. The SSA lectin has a monomer molecular weight of 40 kDa, but forms a tetramer in an aqueous solution. Thus, its molar concentration was calculated with the apparent molecular weight defined as 160 kDa. The "serum Tf" is a Tf present in serum. Tf-2 present in spinal fluid is considered to be also derived from serum. In the subsequent experiments, both serum Tf and Tf-2 were therefore used as positive controls.

Figure 15:
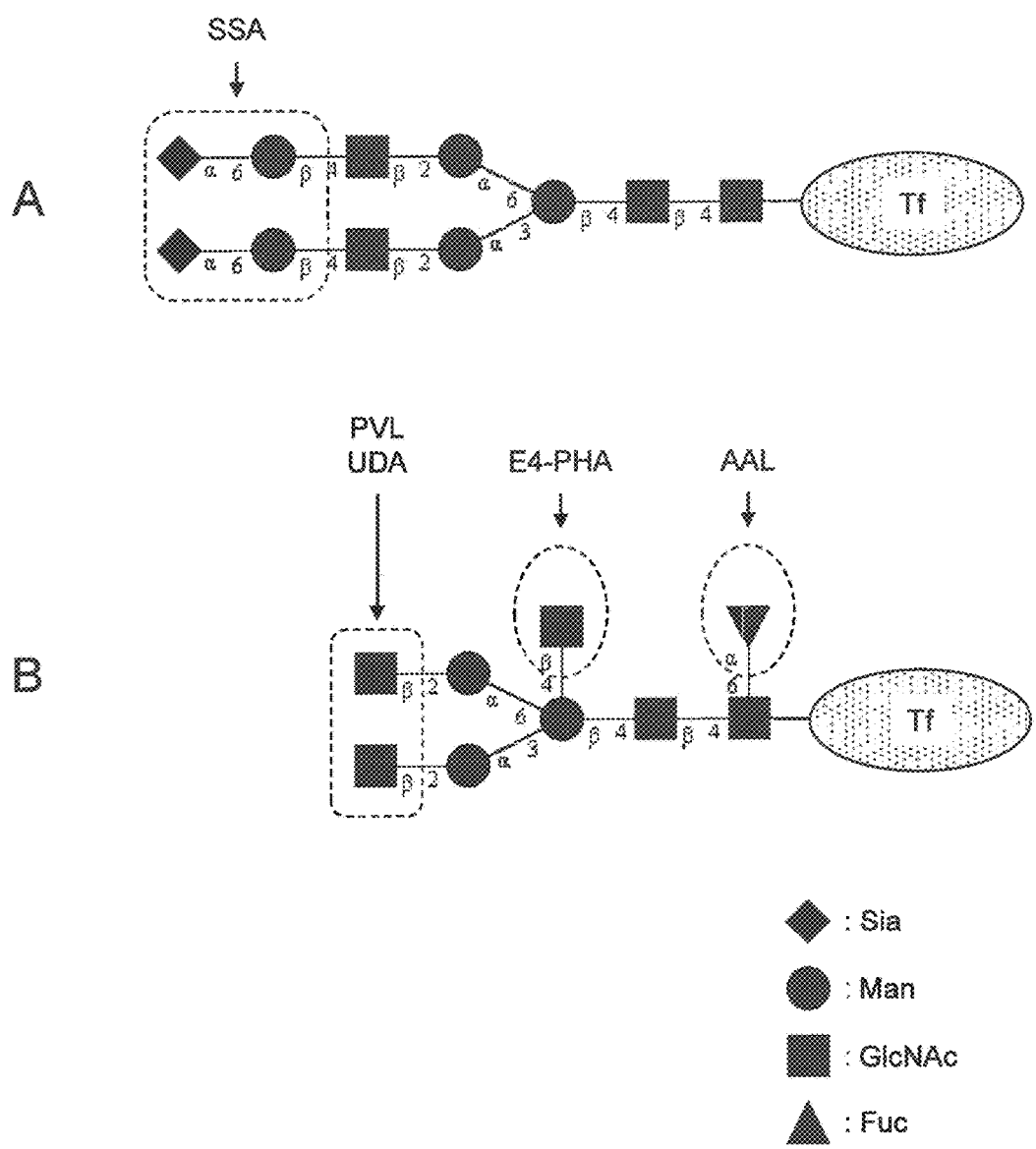
FIG. 15 shows the structures of two types of glycan-isoforms of glycoprotein transferrin in human spinal fluid.

Human spinal fluid transferrin having a sugar chain was used as the glycan-isoform to be assayed. The human spinal fluid transferrin (Tf) includes two types of glycan-isoforms; Tf-2 having a biantennary complex-type sugar chain structure, as with serum Tf as shown in FIG. 15A; and Tf-1 as shown in FIG. 15B. Each glycan-isoform was completely purified and used as a preparation. The glycan-isoform Tf-2 has a sialic acid α2,6-linked galactose structure (Siaα2,6Gal structure) at the non-reducing end. This Siaα2,6Gal structure serves as a binding epitope for SSA lectin, SNA lectin, and TJA-I lectin. On the other hand, unlike the glycan-isoform Tf-2, the glycan-isoform Tf-1 has a N-acetylglucosamine structure (GlcNAc structure) at the non-reducing end, as shown in FIG. 15B. This GlcNAc structure serves as a binding site for PVL lectin and UDL lectin. Tf-1 further has a bisect GlcNAc structure and a core fucose structure in the proximal sugar chain. These structures serve as binding sites for E4-PHA lectin and AAL lectin, respectively.

Thus, whether or not the binding of the anti-human Tf antibody to Tf-1, Tf-2, and serum Tf could be inhibited by the binding of each lectin was tested by ELISA.
(Results)

Figure 3:
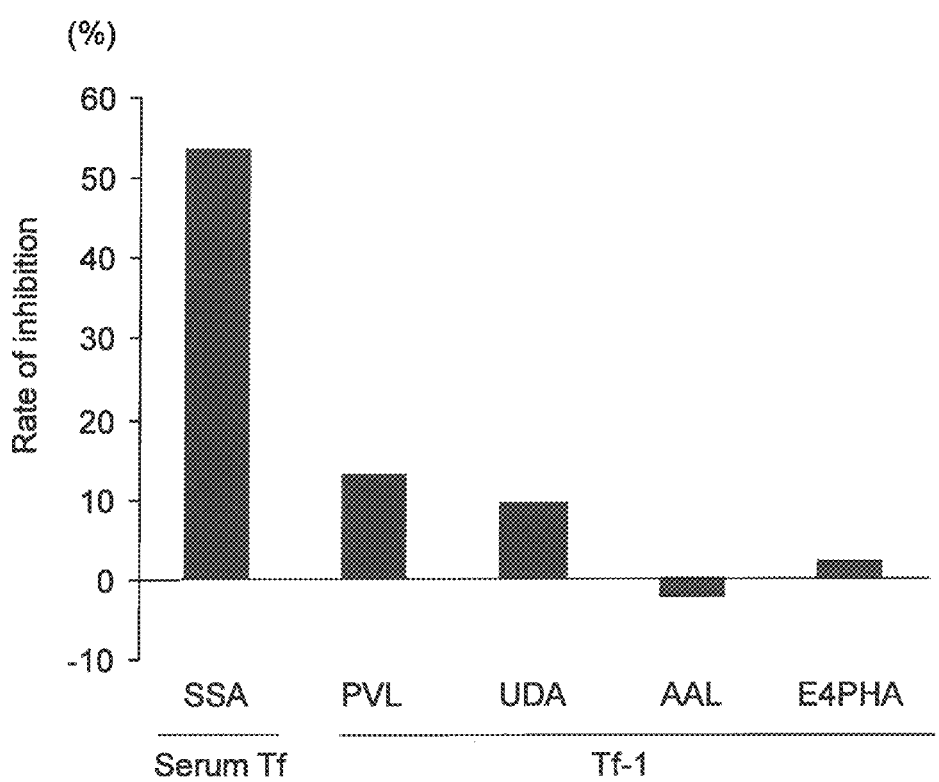
FIG. 3 is a diagram showing the inhibition of immune complex formation by a sugar chain non-reducing terminal residue-binding lectin. The ordinate depicts the rate of inhibition with respect to a control. The abscissa depicts serum Tf and Tf-1, which is an isoform characteristic of spinal fluid. The symbols such as SSA, PVL, and UDA each represent a lectin mixed with the glycan-isoform.

FIG. 3 shows the results of the experiments using Tf-1 and serum Tf. The ordinate of this diagram depicts the rate of inhibition of immune complex formation (the rate of decrease in signals) when the amount of signals from the immune complex in the absence of the competing lectin (in the presence of BSA) was defined as 100%. As shown in FIG. 3, the amount of signals from the serum Tf immune complex was inhibited by 54% in the presence of SSA lectin, which is a sugar chain non-reducing terminal residue-binding lectin. Likewise, the amount of signals from the Tf-1 immune complex was inhibited by 9 and 13% in the presence of PVL and UDA lectins, respectively, which are also sugar chain non-reducing terminal residue-binding lectins. This indicates that when the lectin binding to sugar chain non-reducing terminal residue(s) binds to the sugar chain, the binding of the competing antibody to the core protein (here, Tf) is inhibited. On the other hand, AAL and E4PHA lectins rarely inhibited the amount of signals from the Tf-1 immune complex. This indicates that even if a lectin binding to a proximal sugar chain binds to the sugar chain as shown in the conventional theory, the binding of the competing antibody to the core protein is not inhibited in general.

Example 2: Relation of Inhibition of Immune Complex Formation to Lectin Binding (Purpose)
A test was conducted to verify that the inhibition of immune complex formation shown in Example 1, i.e., the inhibition of antibody binding to the core protein, was brought about by the sugar chain-specific binding of the sugar chain non-reducing terminal residue-binding lectin to the glycan-isoform.
(Method)
Sialic acid in the Siaα2,6Gal structure at the non-reducing end of serum Tf was removed with sialidase to prepare asialo-Tf having terminal galactose. The exposed galactose was further removed by galactosidase treatment to prepare asialo-agalacto-Tf having terminal GlcNAc. SSA lectin can bind to sialic acid at the non-reducing end, but cannot bind to asialo-Tf and asialo-agalacto-Tf.

Figures 1, 4:
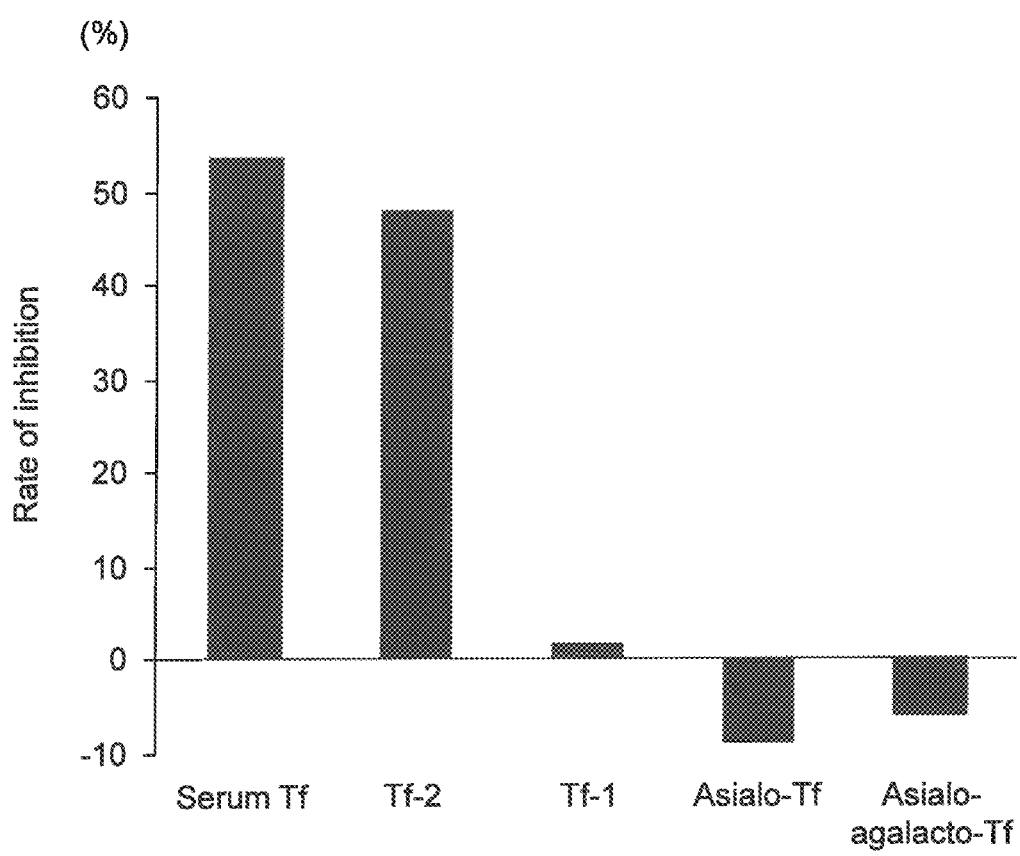
Figures 2, 4:
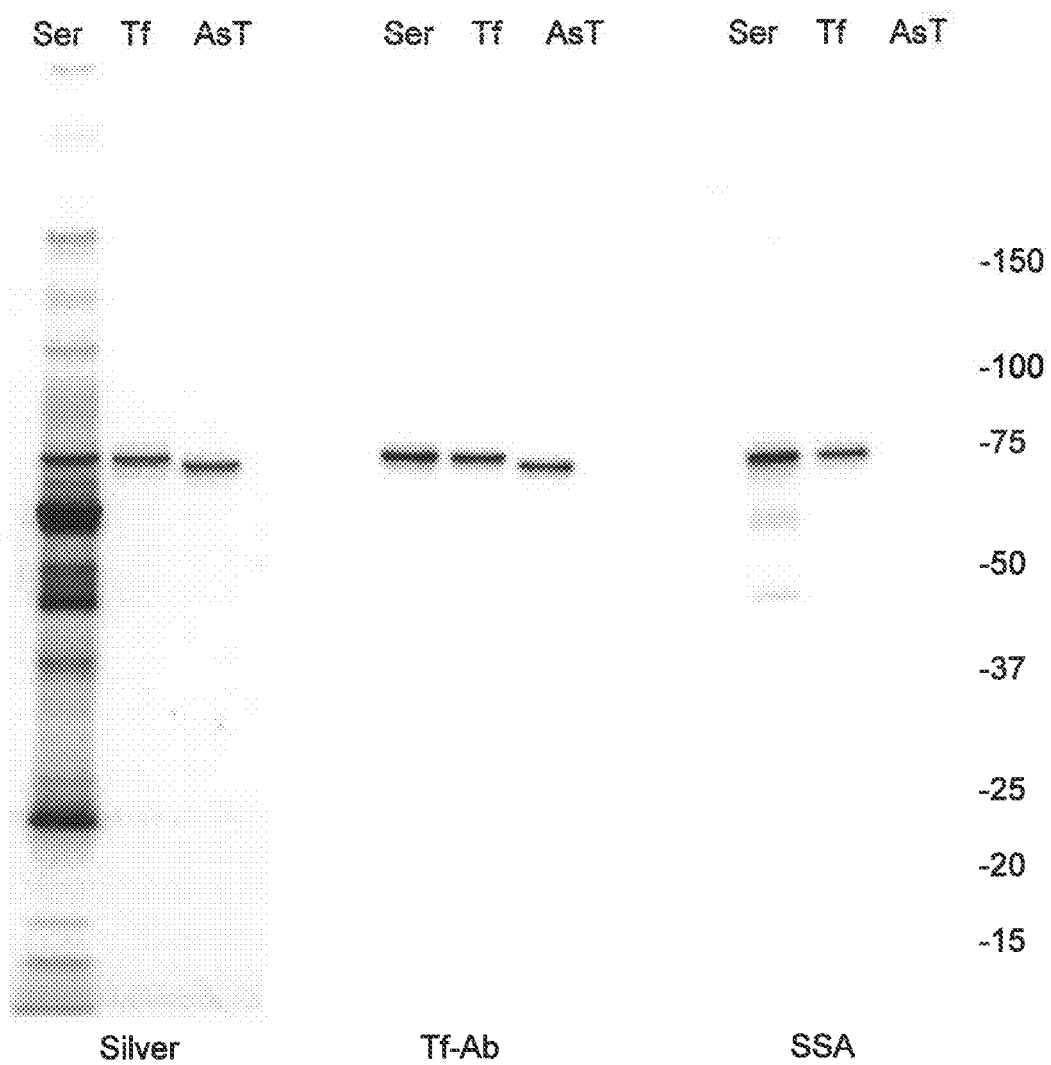

<Inhibition of Immune Complex Formation>
The antibody binding inhibition experiment, i.e., the immune complex formation inhibition experiment, was basically conducted according to the method described in Example 1. Tf-2 and serum Tf having a Siaα2,6Gal structure at the sugar chain non-reducing end were used as samples for positive control. Tf-1 having a GlcNAc structure at the sugar chain non-reducing end was used as a sample for negative control.
<Gel Electrophoresis Analysis>
In gel electrophoresis analysis, 5 to 20% gradient gels (Wako Pure Chemical Industries, Ltd.) of 0.0075 μL/lane of serum Tf, 30 ng/lane of Tf-2, or 30 ng/lane of AsT were used as samples. After electrophoresis at 300 V and 350 mA for 45 minutes using a Tris-glycine buffer, reactivity with transferrin and asialo-transferrin was tested by silver staining, Western blot, and lectin blot. A goat anti-human transferrin antibody (A80-128P, Bethyl Laboratories, Inc.; hereinafter, abbreviated to an "anti-human Tf antibody"; Tf DAKO(+) 1:3000, 120-2(+) IBL; 1:500, 596-3(+) IBL; 1:500) was used in the Western blot. Also, an SSA lectin probe (SSA-bio, Seikagaku Corp.; 1:1000) was used in the lectin blot.
(Results)
The results are shown in FIG. 4.
FIG. 4-1 shows the rate of inhibition of immune complex formation. 54 and 48% inhibitions of immune complex formation were observed in serum Tf and Tf-2, respectively, which are glycan-isoforms capable of binding to SSA lectin. Thus, the results of Example 1 were reproduced. On the other hand, the inhibition of immune complex formation was almost lost in asialo-Tf and asialo-agalacto-Tf that were no longer capable of binding to SSA lectin by the removal of the sugar chain terminal structure of Tf having α2,6-sialic acid. These results demonstrated that the inhibition of immune complex formation confirmed in Tf having α2,6-sialic acid is based on the binding of SSA to the Siaα2,6Gal structure present at the non-reducing end of the Tf sugar chain.

Figure 2:
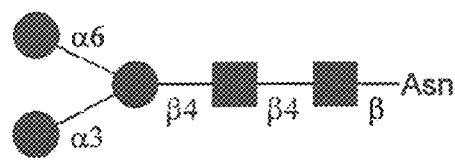
FIG. 2 is a diagram showing a core sugar chain in the glycan-isoform of the present invention.
Figure 2:
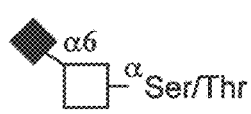
Figure 2:
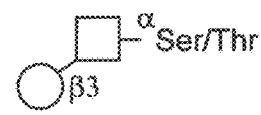
Figure 2:
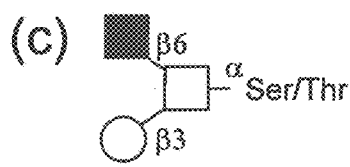
Figure 2:
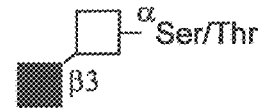
Figure 2:
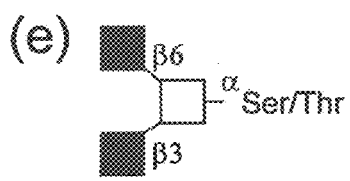
Figure 2:
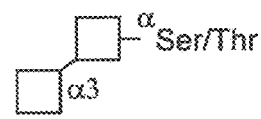
Figure 2:
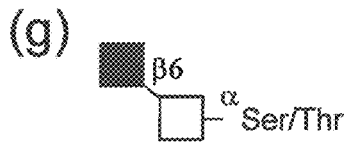
Figure 2:
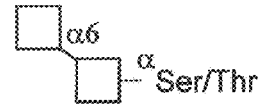
Figure 2:
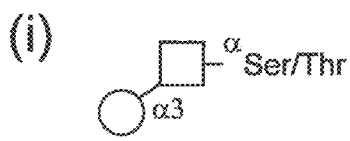

FIG. 4-2 shows the results of the gel electrophoresis analysis. In the diagram, Ser represents Tf in serum, Tf represents purified Tf and AsT represents asialo-Tf. In the silver staining (Silver), Tf in serum, purified Tf, and asialo-Tf were each detected. The asialo-Tf exhibited a slightly lower Rf value than that of Tf in serum or purified Tf. In the Western blot (Tf-Ab) using the anti-human Tf antibody, Tf in serum, purified Tf, and asialo-Tf exhibited almost the same reactivity as in the silver staining. On the other hand, in the lectin blot (SSA), the lectin reacted with serum Tf and Tf but did not react with asialo-Tf, reconfirming that the sialic acid was removed.

Example 3: Test on Universality of Inhibition of Immune Complex Formation (Purpose)
A test was conducted to verify that the similar inhibition of immune complex formation by the sugar chain non-reducing terminal residue-binding lectin could be observed even by use of a capture antibody different from the capture antibody (anti-human Tf antibody) used in Example 1.
(Method)
A rabbit anti-human Tf antibody from Dako Japan Inc. (cat. No. A0061) was used as a capture antibody instead of the anti-human Tf antibody from Cappel Laboratories, Inc. used in Example 1. Also, SSA was used as the lectin. For samples, serum Tf and Tf-2 were used as positive samples, and Tf-1 was used as a negative sample. The specific method followed the method described in Example 1.

(Results)

Figure 5:
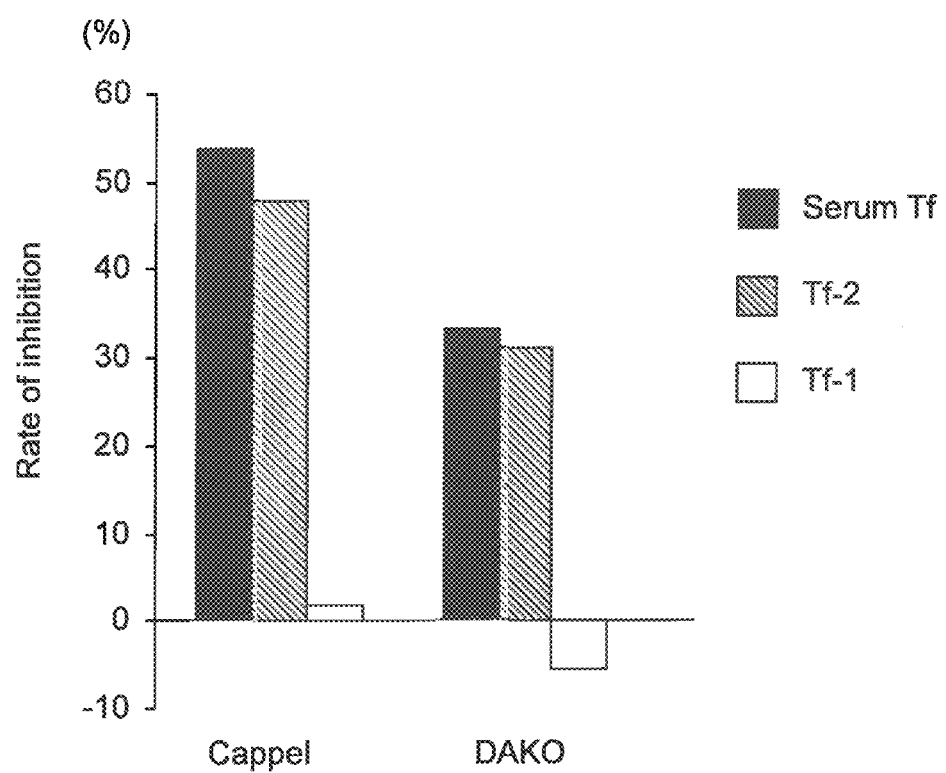
FIG. 5 is a diagram showing the inhibition of immune complex formation when a commercially available anti-human Tf antibody from another manufacturer (Dako Japan Inc.) was used.

The results are shown in FIG. 5. Even in the case of using either of the anti-human Tf antibodies from Cappel Laboratories, Inc. and Dako Japan Inc., the inhibition of immune complex formation was observed in serum Tf and Tf-2. On the other hand, the inhibition of immune complex formation was not observed in Tf-1, as in Example 2. These results demonstrated that the inhibition of complex formation between Tf and the anti-human Tf antibody based on the binding of SSA lectin observed in Examples 1 and 2 is found universal and does not depend on the lot of the antibody used.

Example 4: Relationship Between Concentration of Lectin and its Inhibitory Effect on Immune Complex Formation (Purpose)

The inhibitory effect on immune complex formation was tested for its lectin concentration dependence.

(Method)

Each SSA (300177, Seikagaku Corp.) prepared at varying concentrations within the range of 6.2 pM to 186 nM was added to serum Tf. Then, the rate of inhibition of immune complex formation with the anti-human Tf antibody was measured. The specific method followed the method described in Example 1.

(Results)

Figure 6:
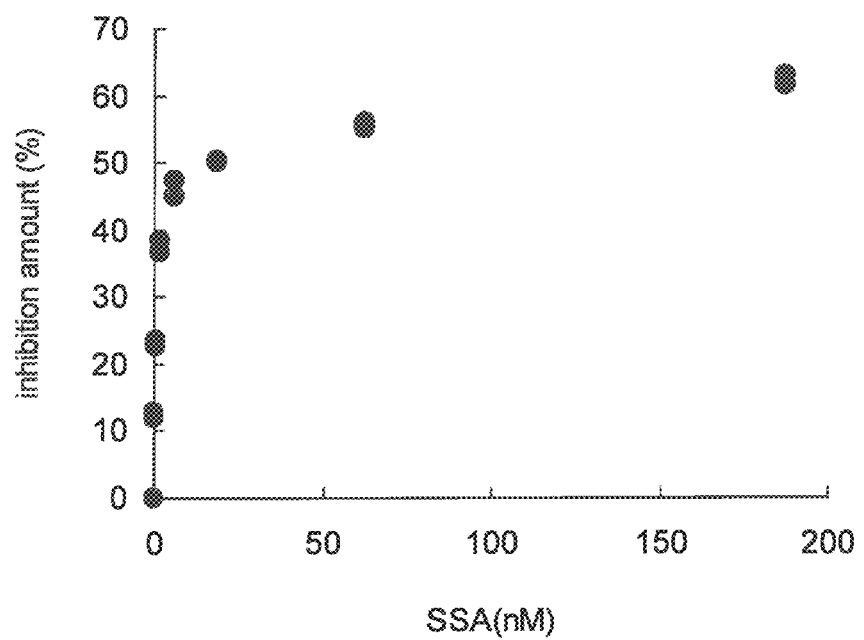
FIG. 6 is a diagram showing an SSA concentration curve for an inhibitory effect.

The results are shown in FIG. 6. The ordinate depicts the rate of inhibition of immune complex formation (rate of decrease in signals) when the amount of signals from the immune complex in the presence of BSA that was used as a control instead of SSA and added at the same concentration there as was defined as 100% in the same way as in Example 1. In the range of 0.2 to 6.2 nM as the concentrations of SSA, the rate of inhibition was increased in a concentration-dependent manner. At the high concentrations equal to or higher than 62 nM, the rate of inhibition was almost in the steady (saturated) state. On the other hand, no inhibitory effect was seen by the addition of BSA within the overall concentration range from 6.2 pM to 186 nM. From these results, the standard conditions for SSA addition were set to 186 nM.

Figure 7:
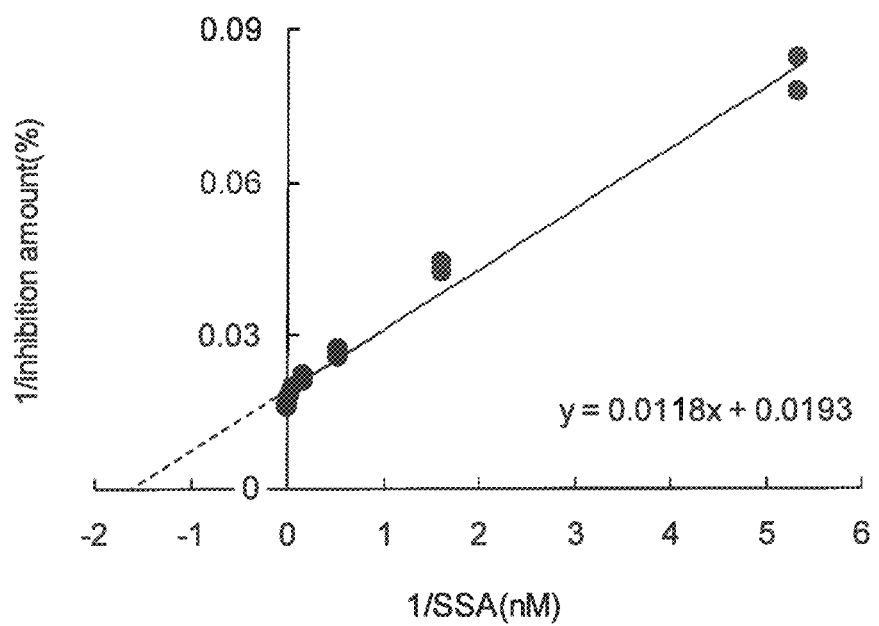
FIG. 7 is a diagram showing a double-reciprocal plot calculated from the concentration curve of FIG. 6.

In order to determine the maximum rate of inhibition (Inhibition max. %) under the aforementioned experimental conditions, a double-reciprocal plot shown in FIG. 7 was prepared. As shown in FIG. 7, Inhibition max. % was calculated as approximately 60%, because the point of intersection with the x-intercept exhibited −1/Inhibition max. %.

Figure 8:
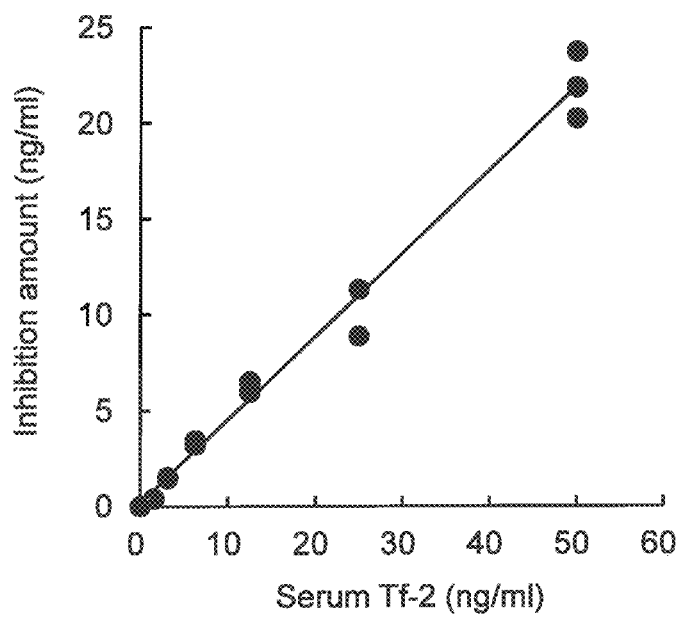
FIG. 8 is a diagram showing a calibration curve for quantifying Tf having terminal α2,6-sialic acid under conditions described in Example 4.

A calibration curve obtained when serum Tf was used as a preparation under the aforementioned experimental conditions is shown in FIG. 8. The calibration curve showed linearity at least within the range of 3 to 50 ng/mL.

Example 5: Correlation Between Tf Index Values of Conventional Detection Method (Western Blot) and Detection Method of the Present Invention (Purpose)

Transferrin isoforms in unpurified spinal fluid were assayed both by the conventional detection method and by the detection method of the present invention to verify the correlation between the Tf index values (Tf-2/Tf-1) obtained in these methods.

(Method)

In the conventional method, Tf-1 and Tf-2 were detected by Western blot as described in JP Patent Publication (Kokai) No. 2010-121980 A (2010), and their concentrations were determined. As a result, reduction in Tf-1 concentration was shown in iNPH. In order to utilize Tf-2 as an internal standard, the ratio of Tf-2 to Tf-1 ([Tf-2]/[Tf-1] ratio) was used as a Tf index value for a diagnostic marker.

On the other hand, in the present invention, the concentration of Tf-2 in unpurified spinal fluid was measured using the calibration curve of FIG. 8 by the method of Example 1. Since 90% or more rate of recovery was obtained in the spike recovery experiment of serum Tf, contaminants in spinal fluid were shown to have almost no influence. The total amount of Tf (i.e., the sum of Tf-1 and Tf-2) can also be calculated by usual sandwich ELISA. Thus, [Tf-1] is calculated by the subtraction of [Tf-2] from [total amount of Tf (total Tf)]. The Tf index value can therefore be determined. Accordingly, the Tf index value was determined for the same individual by each of the conventional detection method and the detection method of the present invention to examine the correlation therebetween. These assay methods both employed unpurified spinal fluid as a sample.

(Results)

Figure 9:
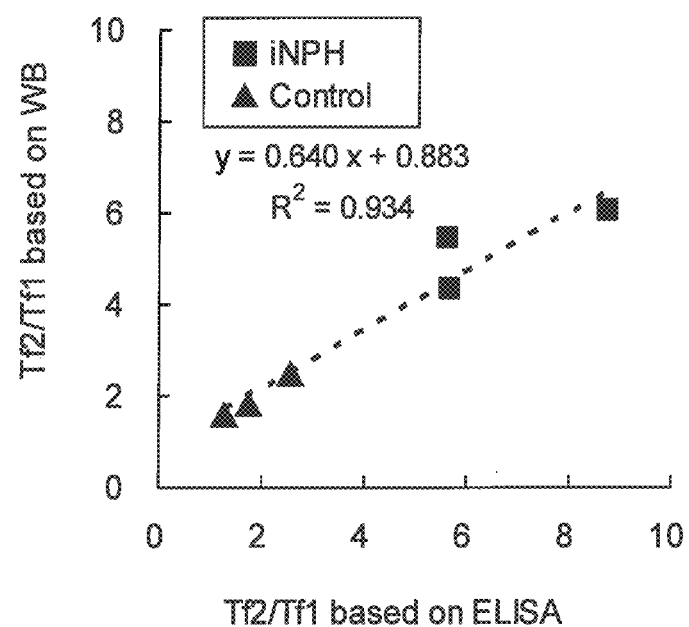
FIG. 9 is a diagram showing the correlation between transferrin index values obtained by a conventional transferrin glycan-isoform detection method (Western blot) and the transferrin glycan-isoform detection method of the present invention ($R^2$=0.934).

The results are shown in FIG. 9. The abscissa depicts the Tf index value obtained by the detection method of the present invention. The ordinate depicts the Tf index value obtained by the conventional Western blot method. As shown in this diagram, the Tf index values of these methods using the unpurified spinal fluid sample exhibited favorable correlation ($R^2$=0.934). These results demonstrated that the detection method of the present invention can serve as a high-throughput glycan-isoform detection method as a substitute for the conventional Western blot method.

Example 6: Inhibitory Effect of Lectin after Immune Complex Formation (Purpose)

In Examples 1 to 5 described above, the sugar chain non-reducing terminal residue-binding lectin and the glycoprotein were mixed in advance to initially form a lectin/glycan-isoform complex, followed by reaction with the antibody on the ELISA plate to test the inhibition of immune complex formation. Thus, in this Example, a test was conducted to confirm whether or not the inhibition of immune complex formation could also take place by the addition of the sugar chain non-reducing terminal residue-binding lectin after immune complex formation.

(Method)

The lectin (final concentration: 186 nM) or BSA (85040C, Sigma-Aldrich Corp.) as a negative control (final concentration: 186 nM) is added to the sample, reacted at room temperature for 1 hour, and then added to a plate coated with the antibody in the same way as in Example 1 (serum Tf+SSA→antigen-antibody reaction on the plate). In another experiment reversing the order of addition of SSA, serum Tf is added to a plate in the absence of SSA and reacted at room temperature for 1 hour (serum Tf→antigen-antibody reaction on the plate). After washing three times with TBST, SSA lectin (final concentration: 186 nM) is added thereto and reacted at room temperature for 1 hour. Each well in these plates was washed three times with TBST, followed by reaction with a goat anti-human Tf-HRP-conjugated antibody (A80-128P, Bethyl Laboratories, Inc.) (0.1 µg/ml) for detection. Each well was washed three times with TBST. Then, a coloring reagent TMB Microwell Peroxidase substrate (50-76-00, KPL, Kirkegaard & Perry Laboratories, Inc.) was prepared according to the protocol of the reagent kit and added at a concentration of 100 μL/well to the plate, which was then left standing at room temperature for 10 minutes. The reaction was terminated by the addition of 1 N HCl. Then, the absorbance was measured at 450 nm using a microplate reader (Model 680, Bio-Rad Laboratories, Inc.).
(Results)

Figure 10:
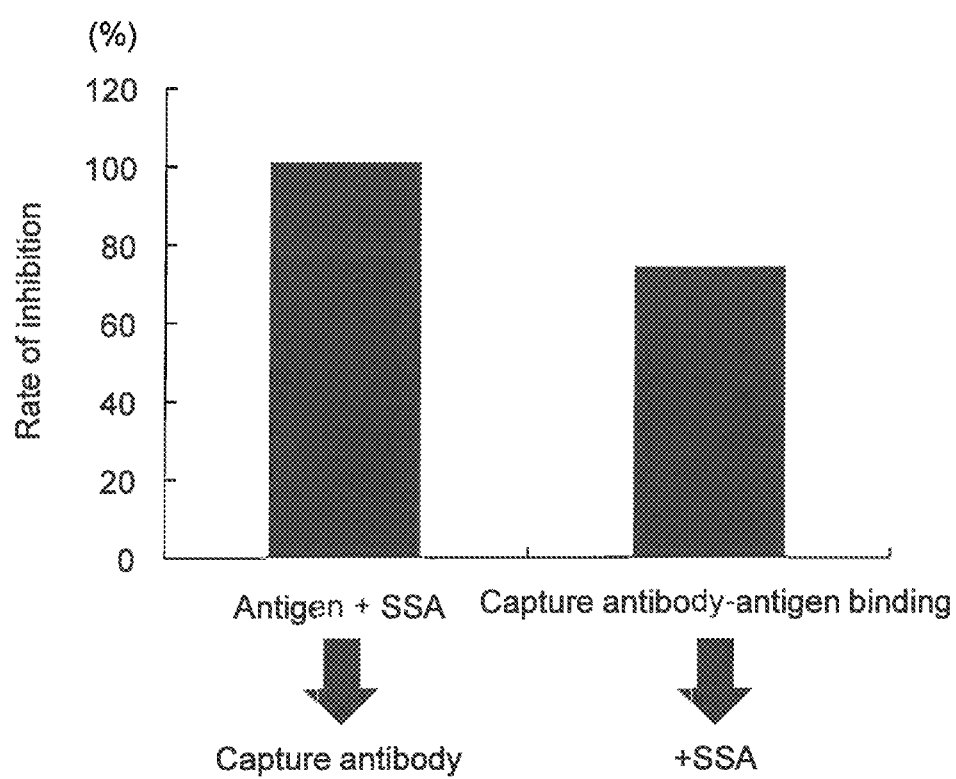
FIG. 10 is a diagram showing an immune complex formation inhibitory effect brought about by the mixing of a sugar chain non-reducing terminal residue-binding lectin after immune complex formation.

The results are shown in FIG. 10. These results showed that the detection is achieved regardless of the order of addition of the lectin, though the rate of inhibition (41%) in the method of adding SSA lectin after antigen-antibody reaction was slightly lower than the rate of inhibition (54%) in the method of reacting the antibody after binding of between SSA lectin and serum Tf in advance. This demonstrated that the inhibition of immune complex formation by the sugar chain non-reducing terminal residue-binding lectin takes place regardless of the order in which the sugar chain non-reducing terminal residue-binding lectin and the antibody are mixed with the glycoprotein.

Example 7: Verification of Glycan-Isoform Detection Method of the Present Invention Using Immunoprecipitation (Purpose)

In Examples 1 to 6 described above, the inhibition of immune complex formation by the sugar chain non-reducing terminal residue-binding lectin was detected by ELISA. A test was conducted to confirm whether or not the inhibition could also be detected by the immunoprecipitation method.
(Method)

Protein G-Sepharose beads (GE, 17-0618-02) were blocked with 0.1% BSA+TBST at room temperature for 1 hour. Subsequently, an anti-human Tf antibody solution (Cappel #55045, 18.6 μg/mL) treated with periodate in the same way as in Example 1 was added thereto. After stirring for 1 hour or longer, the beads were washed with TBST to remove bead-unbound antibodies and thereby prepare antibody beads. Next, 300 μg of SSA or the same amount of BSA was added to 1 μg of serum Tf and reacted at room temperature for 1 hour. After the reaction, 10 μL of the antibody beads (50% suspension) was added thereto and reacted at 4° C. for 2 hours (total volume: 500 μL). After the reaction, the supernatant was separated from the beads by centrifugation. Unabsorbed Tf is contained in this supernatant. 8 μL of each recovered supernatant was mixed with 2 μL of Laemmli sample buffer (5-fold concentration). Then, SDS/PAGE was conducted using 7.5% polyacrylamide gel. After electrophoresis at a constant current of 20 mA for 70 minutes, the separated protein was electrically transferred to a nitrocellulose membrane at a constant current of 350 mA for 45 minutes. After the transfer, the nitrocellulose membrane was blocked with 3% skimmed milk-0.1% Tween 20-PBS (phosphate buffered saline) for 1 hour or longer. The nitrocellulose membrane was reacted for 2 hours with a goat anti-human Tf antibody (Bethyl Laboratories, Inc., A80-128A) (0.5 μg/mL) diluted to 1:2000 with 3% skimmed milk-0.1% Tween 20-PBS. The nitrocellulose membrane was washed three times (10 minutes for each operation) with 0.1% Tween 20-PBS and then reacted for 1 hour with an anti-goat IgG HRP-conjugated antibody (Jackson, 705-035-147) (0.5 μg/mL) diluted to 1:2000 with 3% skimmed milk-0.1% Tween 20-PBS. The nitrocellulose membrane was washed again three times (10 minutes for each operation) with a washing solution. The band of Tf was detected in a CS analyzer (Cool Saver: ATTO Corp.) using a chemiluminescent substrate (Pierce SuperSignal West Dura Extended Duration Substrate).
(Results)

Figure 11:
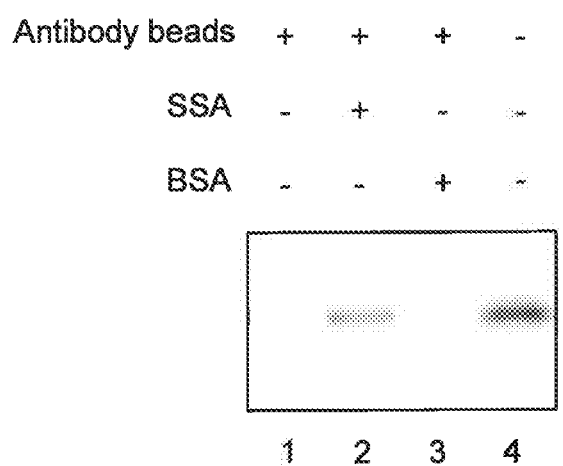
FIG. 11 is a diagram showing that serum Tf contained in a supernatant after immunoprecipitation using anti-human Tf antibody-immobilized beads was detected by Western blot.

The results are shown in FIG. 11. When SSA or BSA is not added, Tf is rarely detected in the supernatant, because the majority of serum Tfs are precipitated through the binding to the antibody beads (lane 1). By contrast, when 300 μg of SSA was mixed into this reaction system, Tf was detected in the supernatant (lane 2). On the other hand, when BSA was added thereto, Tf was not detected in the supernatant (lane 3). These results demonstrated that the immune complex formation can also be inhibited by the sugar chain non-reducing terminal residue-binding lectin in the immunoprecipitation method using antibody beads.

Example 8: Inhibitory Effect of SSA Lectin in α2-Macroglobulin Assay (Purpose)

In Examples 1 to 7, all of the core proteins were Tf. Thus, a test was conducted to verify that the inhibition of immune complex formation by the presence of the sugar chain non-reducing terminal residue-binding lectin could also take place for glycan-isoforms having other core proteins.
(Method)

Serum α2-macroglobulin, which is a serum glycoprotein, was used as a test sample. The serum α2-macroglobulin (Siaα2M) has a sugar chain containing a Siaα2,6Gal structure as a SSA-binding site at the non-reducing end, as with serum Tf. Accordingly, the serum α2-macroglobulin, asialo-α2-macroglobulin obtained by the sialidase treatment of the serum α2-macroglobulin, and asialo-agalacto-α2-macroglobulin obtained by the further galactosidase treatment thereof were used in the same sandwich ELISA assay method as in Examples 1 and 2 to study the inhibitory effect of SSA lectin on immune complex formation. The assay method followed the method described in Examples 1 and 2 except that: 10 ng of purified human α2-macroglobulin (Sigma #M6159) was used as the glycan-isoform of interest; a goat anti-human α2-macroglobulin antibody (Cappel #55113) treated with periodate was used as a capture antibody; and a goat anti-human α2-macroglobulin antibody (GeneTex #GTX27339) was used as an antibody for detection.
(Results)

Figure 12:
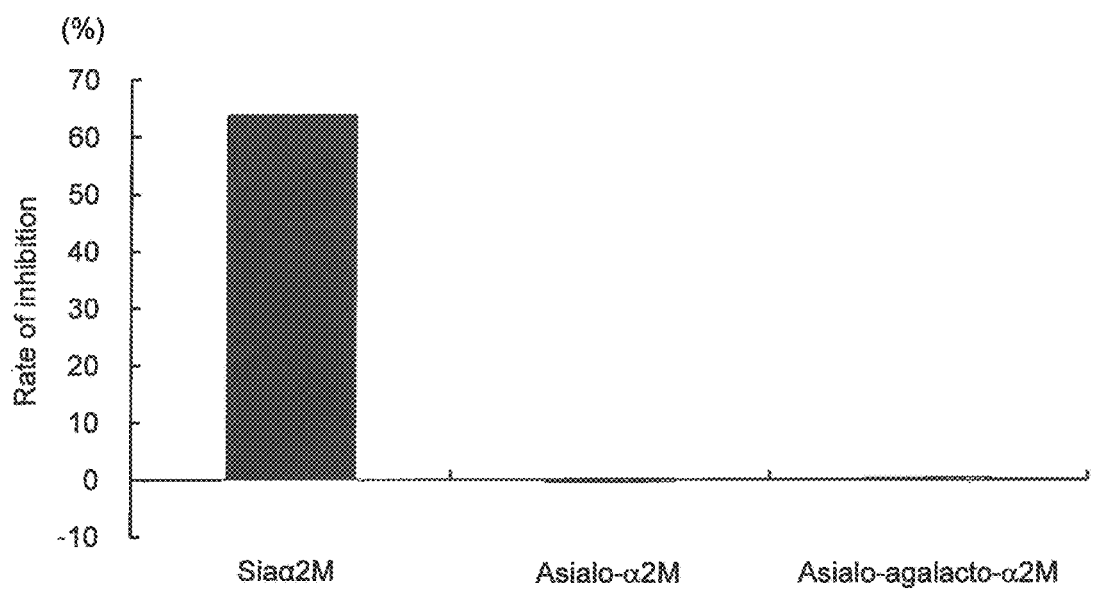
FIG. 12 shows the assay of α2-macroglobulin having α2,6-sialic acid as a terminal sugar chain.

The results are shown in FIG. 12. When ELISA signals obtained by the addition of BSA were defined as 100%, approximately 65% ELISA signals were inhibited by the addition of SSA. On the other hand, the inhibition of ELISA signals by SSA was not observed in asialo-α2-macroglobulin and asialo-agalacto-α2-macroglobulin. These results were consistent with the results of Examples 1 and 2. These results demonstrated that the inhibition of immune complex formation by the non-reducing end-binding lectin is a universal phenomenon that occurs even when the core protein is a protein other than Tf.

Example 9: Immunohistochemistry of N-Glycan Glycan-Isoform—(1)

(Purpose)

The glycan-isoform detection method of the present invention was immunohistochemically tested for its applicability to glycan-isoforms on pathology-free tissue sections.

(Method)

For pathological autopsy cases, a portion of the pathology-free liver fixed in formalin was collected. Each liver sample was embedded in paraffin, and continuous sections of 5 μm in thickness were prepared. Each tissue section was extended on aminosilane-coated slide glass (Matsunami Glass Ind., Ltd.) and attached thereto. Subsequently, the tissue section was deparaffinized with xylene, and this xylene was subsequently washed off with ethanol. The tissue section was washed with a phosphate buffer solution (100 mM phosphate buffered saline; PBS) and then left standing for 20 minutes in 0.3% hydrogen peroxide-methanol solution. The tissue section was washed with PBS and then treated with microwave for 10 minutes in a citrate buffer solution. After the antigen retrieval in the tissue, the tissue section was cooled at room temperature. The tissue section was washed with PBS. For competition with an anti-Tf antibody, 40 μg/mL SSA lectin solution prepared in advance was then added dropwise onto the tissue in an amount that permitted sufficient covering of the tissue. A BSA solution (40 μg/mL) was used as a control for the lectin. The tissue section thus treated was held in a humid box and left standing overnight at 4° C.

Next, an anti-human Tf rabbit IgG antibody (Dako Japan Inc.) serving as a capture antibody (primary antibody) was treated with periodate according to the method described in Example 1 and then added dropwise at a dilution ratio of 1:1000 to the tissue section onto which the lectin solution had been added dropwise, followed by overnight reaction at 4° C. A capture antibody-bound region on the tissue section was visualized by staining using a biotin-labeled anti-rabbit IgG antibody (Histofine SAB-PO®, Nichirei Corp.) serving as an antibody for detection (secondary antibody) and Simple Stain-DAB solution. The tissue section thus stained was washed with running water and subjected to nuclear staining using 2% aqueous Methyl Green solution. The tissue section was dehydrated with ethanol and penetrated using xylene. Then, an encapsulant (Bioleit, Okenshoji Co., Ltd.) was added dropwise thereto, and the tissue section was mounted on cover glass and observed under a microscope (DZ9000, Keyence Corp.).

In order to further confirm immunohistochemically that the inhibition of immune complex formation by lectin depended on sialic acid, the tissue section was treated with sialidase. The specific treatment conditions followed those described in Example 2.

(Results)

Figures 1, 13:
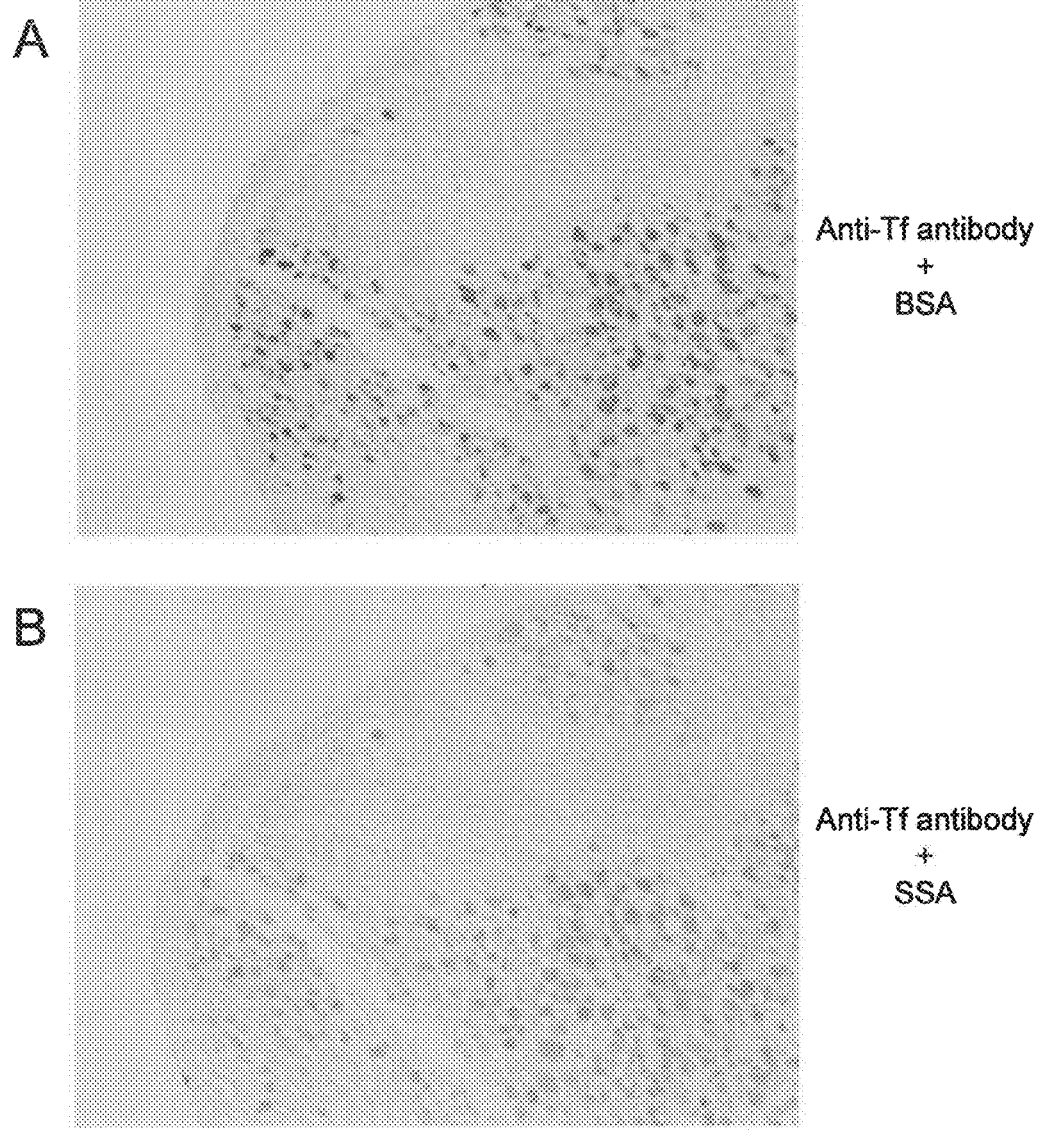
Figures 2, 13:
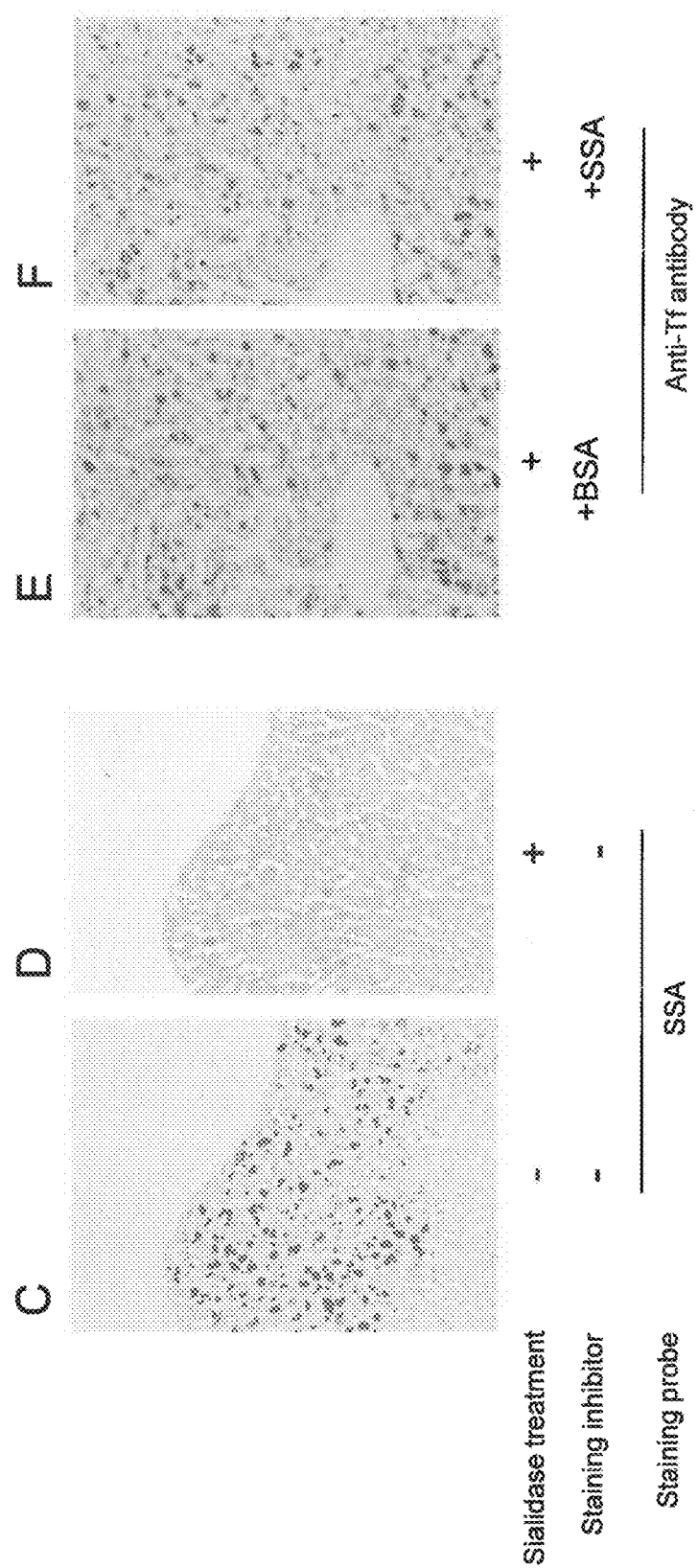

The results are shown in FIG. 13.

FIG. 13-1 shows the results about the inhibition of immune complex formation by the lectin. FIGS. 13-1A and 13-1B show the distribution of Tf on the tissue sections supplemented with BSA and SSA, respectively. From FIGS. 13-1A and 13-1B, serum Tf was shown to be secreted from liver cells. In the tissue section of FIG. 13-1B, evident reduction in immunostaining was seen as compared with the control tissue section of FIG. 13-1A. These results indicate that SSA inhibited the formation of the immune complex between serum Tf (SSA-binding Tf) present in the tissue and the capture antibody. Specifically, these results demonstrated that the N-glycan-isoform detection method of the present invention is also applicable to the immunohistochemistry.

FIG. 13-2 shows the results about the SSA lectin staining and immunohistochemistry of the sialidase-treated section. FIG. 13-2C shows the tissue section before the sialidase treatment, and FIGS. 13-2D, 13-2E, and 13-2F show the liver tissue sections after the sialidase treatment. FIGS. 13-2C and 13-2D or FIGS. 13-2E and 13-2F show the corresponding liver tissue sections. FIGS. 13-2C and 13-2D depict the results about the SSA lectin staining, and FIGS. 13-2E and 13-2F depict the results about the anti-human Tf antibody staining. In FIGS. 13-2C and 13-2D, the α2,6-sialic acid residue on the liver tissue section before the sialidase treatment (FIG. 13-2C) was detected, whereas the signals of the α2,6-sialic acid residue mostly disappeared after the sialidase treatment (FIG. 13-2D), demonstrating that the sialic acid on the liver tissue section was removed. On the other hand, in FIGS. 13-2E and 13-2F, strong signals of Tf were observed by the addition of SSA (FIG. 13-2F), as in the addition of BSA (FIG. 13-2E), because the α2,6-sialic acid residue was removed by the sialidase treatment. In this case, the inhibitory effect of the lectin was not confirmed. This indicates that the removal of the sugar chain terminal sialic acid of Tf by the sialidase treatment cancelled the inhibition of immune complex formation by SSA lectin. These immunohistochemical results also demonstrated that the binding of SSA lectin to the α2,6-sialic acid residue is essential for the inhibition of immune complex formation of the anti-Tf antibody by the SSA lectin.

Example 10: Immunohistochemistry of O-Glycan Glycan-Isoform (Purpose)

The glycan-isoform detection method of the present invention was immunohistochemically tested for its applicability to O-glycan glycan-isoforms on pathology-free tissue sections.

(Method)

For pathological autopsy cases, a portion of the pathology-free colon fixed in formalin was collected. Colon sections were prepared in the same way as in Example 9. Each tissue section was extended on aminosilane-coated slide glass (Matsunami Glass Ind., Ltd.) and attached thereto. In this example, a series of two mirror sections (the first section of the continuous sections was attached upside down onto slide glass, and the next section was attached as it was) were also prepared. The tissue section was washed with PBS. Then, 40 μg/mL WFA lectin solution prepared in advance was added dropwise onto the tissue in an amount that permitted sufficient covering of the tissue. A BSA solution (40 μg/mL) was used as a control for the lectin. The tissue section thus treated was held in a humid box and left standing overnight at 4° C.

Next, an anti-sialyl MUC1 antibody (Takeuchi, H. et al., Journal of Immunological Methods. 2002, 270: 199-209) serving as a capture antibody (primary antibody) was added dropwise at a dilution ratio of 1:1000 to the tissue section onto which the lectin solution had been added dropwise, followed by overnight reaction at 4° C. A capture antibody-bound region on the tissue section was visualized by staining using a biotin-labeled anti-mouse IgG antibody (Histofine SAB-PO®, Nichirei Corp.) serving as an antibody for detection (secondary antibody) and Simple Stain-DAB solution. The tissue section thus stained was washed with running water and subjected to nuclear staining using 2% aqueous Methyl Green solution. The tissue section was dehydrated with ethanol and penetrated using xylene. Then, an encapsulant (Bioleit, Okenshoji Co., Ltd.) was added dropwise thereto, and the tissue section was mounted on cover glass and observed under a microscope (DZ9000, Keyence Corp.).

(Results)

Figure 14:
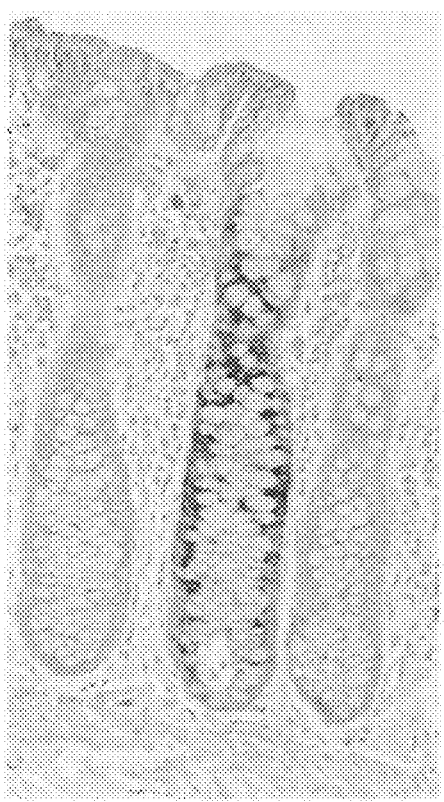
FIG. 14 shows the detection of MUC1 having a WFA-binding sugar chain in the human colon.
Figure 14:
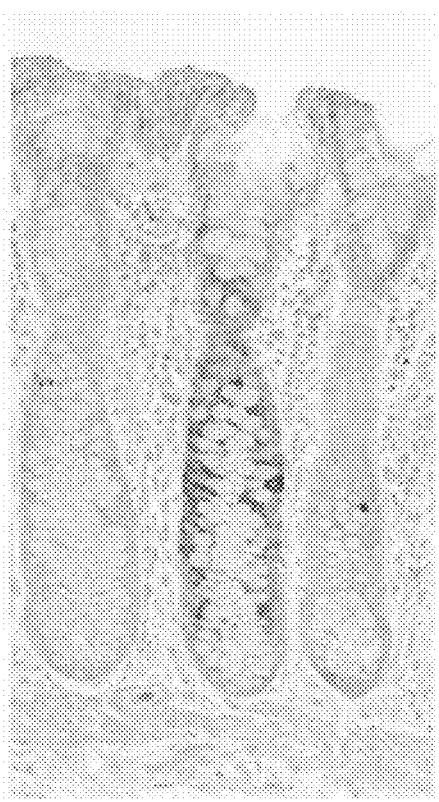

The results are shown in FIG. 14. Sialyl MUC1 is secreted from some colonic goblet cells. FIGS. 14A and 14B show the signals of the anti-sialyl MUC1 antibody on the tissue sections upon action of BSA and WFA, respectively. Reduction in staining signals was seen in the tissue section of FIG. 14B as compared with the control tissue section of FIG. 14A. These results indicate that WFA inhibited the formation of the immune complex between sialyl MUC1 (WFA-binding sialyl MUC1) present in the tissue and the anti-sialyl MUC1 antibody. Specifically, these results demonstrated that the O-glycan glycan-isoform detection method of the present invention is also applicable to the immunohistochemistry.

Example 11: Immunohistochemistry of N-Glycan Glycan-Isoform—(2)

(Purpose)

The glycan-isoform detection method of the present invention was immunohistochemically tested for its applicability to N-glycan glycan-isoforms on cancer tissue sections manifesting pathology.

(Method)

An antibody (anti-CEA antibody) against carcinoembryonic antigen (hereinafter, abbreviated to "CEA") was used as an antibody. CEA has diverse sugar chain structures with the attachment of 25 to 28 N-glycans. For example, CEA expressed in the liver metastasis of colon cancer is known to be α2,6-sialylated (Yamashita et al., 1995, Cancer Res 55: 1675-1679). On the other hand, NFA-2, a normal counterpart of CEA, is α2,3-sialylated, suggesting that the expression of α2,6-sialylated CEA correlates with the metastasis of colon cancer. Hence, distal metastases including liver metastasis can be predicted by the detection of α2,6-sialylated CEA in the primary tumor. Also, α2,6-sialylated CEA in serum is useful as a metastatic marker. Thus, α2,6-sialylated CEA serves as a useful marker for recurrent cancer with a distal metastasis in order to determine the presence or absence of the metastasis or to determine a therapeutic strategy appropriate for the status of the metastasis. Although CEA is used in cancer screening, this marker produces false-positive cases in such a way that it exhibits high levels in some smokers, leading to reduction in proper diagnosis rate. Screening having high cancer specificity can be achieved by the detection of α2,6-sialylated CEA.

For surgical cases with colon cancer confirmed to have a rise in serum CEA level, excised colon cancer was fixed in formalin, and a portion thereof was embedded in paraffin. Sectioning and pretreatment were carried out in the same way as in Example 9. The inhibition of immune complex formation by the lectin was tested using an SSA solution (40 μg/mL), as in Example 9. A BSA solution (40 μg/mL) was used as a control for the lectin. SSA recognizes the α2,6-sialic acid epitope.

An anti-CEA antibody (No. 10094, IBL Co., Ltd.) was added dropwise at a dilution ratio of 1:1000 to each section, followed by overnight reaction at 4° C. The immune response of the anti-CEA antibody was visualized by staining using a biotin-labeled anti-mouse IgG antibody (Histofine Universal Kit, Nichirei Corp.) as a secondary antibody. The tissue section thus stained was washed with running water and subjected to nuclear staining using hematoxylin (the nucleus is stained pale purple in an oval shape). Mounting and observation were carried out in the same way as in Example 9.

(Results)

Figure 16:
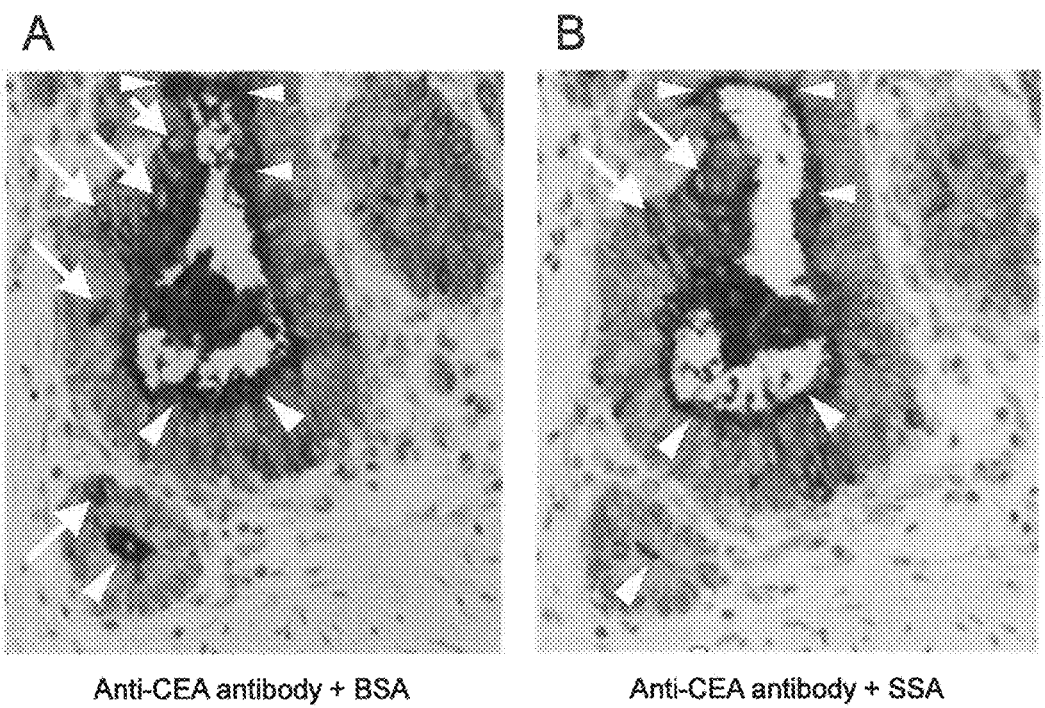
FIG. 16 shows the detection of carcinoembryonic antigen (CEA) having α2,6-sialic acid in a human colon cancer section.

The results of immunostaining CEA in the infiltrated locus of colon cancer is shown in FIG. 16. FIG. 16A shows the BSA-treated section, and FIG. 16B shows the SSA-treated section.

Cells in the infiltrated locus have a relatively high degree of differentiation and maintain a ductal structure. In both of FIGS. 16A and 16B, the signals of CEA were detected, particularly, on the apical side of the cells (arrowheads). Reduction in CEA immunostaining was observed in the SSA-supplemented tissue section of FIG. 16B as compared with the BSA-supplemented control tissue section of FIG. 16A. These results suggest that the majority of CEAs on the apical side had α2,6-sialic acid and underwent the inhibition of staining by SSA.

In FIG. 16A, cells in which the neighborhood of the pale purple nucleus in an oval shape was densely stained was further seen (arrows). This stained image seems to represent intracellular CEA signals. In FIG. 16B under the SSA addition conditions, in spite of the continuous sections, the number of densely stained cells was small, and such cells, if present, were low stainable. Thus, it was shown that the densely stained cells in FIG. 16A are cells having α2,6-sialylated CEA, and its signals were attenuated in the presence of SSA (FIG. 16B). As is evident from these results, the presence of α2,6-sialylated CEA in the infiltrated locus of colon cancer was visualized according to the present invention.

All publications, patents, and patent applications cited herein are incorporated herein by reference in their entirety.

The invention claimed is:

1. A method for detecting a glycan-isoform of interest in a test sample, comprising:
   (i) mixing the test sample, in a buffer or body fluid, with a sugar chain non-reducing terminal residue-binding lectin which binds to the whole, or to a portion of, the sugar chain non-reducing terminal residue(s) in the sugar chain moiety of the glycan-isoform of interest,
   (ii) mixing the test sample with an antibody specifically binding to the protein moiety of the glycan-isoform of interest, to form an immune complex, and wherein the antibody is immobilized on a solid-phase carrier;
   (iii) quantifying an amount of the immune complex of the antibody and the glycan-isoform of interest after the lectin mixing of step (i) and the antibody mixing of step (ii);
   (iv) obtaining a control immune complex by subjecting a control sample to the above steps (i)-(iii), provided that the control sample is not mixed with the sugar chain non-reducing terminal residue-binding lectin; and
   (v) determining the presence or absence of the glycan-isoform of interest in the test sample on the basis of the difference between the amount of the immune complex and an amount of the control immune complex, wherein the sugar chain non-reducing terminal residue(s) in the sugar chain moiety is selected from the group consisting of an α2,6-sialic acid, an α2,3-sialic acid, galactose, GalNAc, GlcNAc, polylactosamine, and a blood group antigen fucose,
   wherein the sugar chain non-reducing terminal residue-binding lectin is selected from the group consisting of an α2,6-sialic acid-binding lectin, an α2,3-sialic acid-binding lectin, a galactose/GalNAc-binding lectin, a GlcNAc-binding lectin, a polylactosamine-binding lectin, and a blood group antigen fucose-binding lectin; and
   wherein the antibody mixing of step (ii) is carried out after the lectin mixing of step (i).

2. The glycan-isoform detection method according to claim 1, wherein the glycan-isoform of interest is present in the test sample when the amount of the immune complex is quantitatively lower than the amount of the control immune complex.

3. The glycan-isoform detection method according to claim 1, wherein the test sample is a tissue section.

4. A method for identifying a glycan-isoform, comprising identifying the glycan-isoform using a glycan-isoform detection method according to claim 1.

5. The glycan-isoform detection method according to claim 1, wherein the α2,6-sialic acid-binding lectin is selected from the group consisting of *Sambucus sieboldiana*-derived agglutinin (SSA), *Sambucus nigra*-derived agglutinin (SNA), and *Trichosanthes japonica*-derived type I agglutinin (TJA-I).

6. The glycan-isoform detection method according to claim 1, wherein the α2,3-sialic acid-binding lectin is *Maackia amurensis*-derived agglutinin (MAL).

7. The glycan-isoform detection method according to claim 1, wherein the galactose/GalNAc-binding lectin is selected from the group consisting of *Erythrina cristagalli*-derived agglutinin (ECA), *Ricinus communis*-derived agglutinin 120 (RCA120), *Bauhinia purpurea*-derived agglutinin (BPL), *Trichosanthes japonica*-derived type II agglutinin (TJA-II), and *Wisteria floribunda*-derived agglutinin (WFA).

8. The glycan-isoform detection method according to claim 1, wherein the GlcNAc-binding lectin is selected from the group consisting of *Psathyrella Velutina* Lectin (PVL), *Urtica dioica* agglutinin (UDA), *Grifonia simplicifolia*-derived agglutinin (GSL-II), and *Agaricus bisporus*-derived agglutinin (ABA).

9. The glycan-isoform detection method according to claim 1, wherein the GlcNAc-binding lectin is selected from the group consisting of GSL-II and ABA.

10. The glycan-isoform detection method according to claim 1, wherein the polylactosamine-binding lectin is *Lycipersicon esculentum*-derived agglutinin (LEL) or *Solanum tuberosum*-derived agglutinin (STL).

11. The glycan-isoform detection method according to claim 1, wherein the blood group antigen fucose-binding lectin is *Lotus tetragonolobus*-derived Agglutinin (LTL) or *Ulex eunpaeus*-derived agglutinin I (UEA-I).

12. The glycan-isoform detection method according to claim 1, wherein the antibody is a monoclonal antibody.

13. The glycan-isoform detection method according to claim 1, further comprising a step of comparing the amounts of the immune complex and the control immune complex between steps (iv) and (v).

* * * * *